(12) United States Patent
Reischig

(10) Patent No.: US 11,073,488 B2
(45) Date of Patent: Jul. 27, 2021

(54) METHOD OF GENERATING A FINGERPRINT FOR A GEMSTONE USING X-RAY IMAGING

(71) Applicant: Peter Reischig, Leicester (GB)

(72) Inventor: Peter Reischig, Leicester (GB)

(*) Notice: Subject to any disclaimer, the term of this patent is extended or adjusted under 35 U.S.C. 154(b) by 535 days.

(21) Appl. No.: 15/534,554

(22) PCT Filed: Dec. 9, 2015

(86) PCT No.: PCT/GB2015/053768
§ 371 (c)(1),
(2) Date: Jun. 9, 2017

(87) PCT Pub. No.: WO2016/092300
PCT Pub. Date: Jun. 16, 2016

(65) Prior Publication Data
US 2017/0343493 A1    Nov. 30, 2017

(30) Foreign Application Priority Data

Dec. 9, 2014  (GB) ...................... 1421837

(51) Int. Cl.
*G01N 23/20*    (2018.01)
*G01N 23/20008*    (2018.01)
(Continued)

(52) U.S. Cl.
CPC ............ *G01N 23/207* (2013.01); *G01N 23/04* (2013.01); *G01N 23/046* (2013.01); *G01N 23/18* (2013.01);
(Continued)

(58) Field of Classification Search
CPC ............ G01N 23/20; G01N 23/20008; G01N 23/20016; G01N 23/20025; G01N 23/201;
(Continued)

(56) References Cited

U.S. PATENT DOCUMENTS 4,125,770 A * 11/1978 Lang ..................... B01J 3/062
356/30
5,077,767 A * 12/1991 Gaukroger .......... G01N 23/205
378/71
(Continued)

FOREIGN PATENT DOCUMENTS

WO    WO-9808081 A2 *  2/1998 .......... G01N 23/207
WO    WO-2006033102 A1 *  3/2006 ............. G01N 21/87

OTHER PUBLICATIONS

Philip M. Martineau et al., Identification of Synthetic Diamond Grown Using Chemical Vapor Deposition (CVD), Gems & Gemology, vol. 40, No. 1, Spring 2004, pp. 2-25.*

(Continued)

*Primary Examiner* — Allen C. Ho
(74) *Attorney, Agent, or Firm* — NK Patent Law

(57) ABSTRACT

The fingerprint comprises a three-dimensional map of internal imperfections present in a crystal within the gemstone (5), and may also comprise further information about the gemstone (5). The method comprises scanning the gemstone in an imaging apparatus by recording diffraction and/or extinction images according to a scanning strategy, and generating a fingerprint from the recorded diffraction and/or extinction images. The imaging apparatus comprises a sample holder (4), a sample stage (3), a detector (6), an x-ray source (1), wherein the sample holder (4) is movable relative to the x-ray source (1) and the detector (6). The fingerprint is used for the identification of gemstones, and/or for tracking and/or processing of gemstones in a supply chain.

21 Claims, 1 Drawing Sheet

Figure 1:
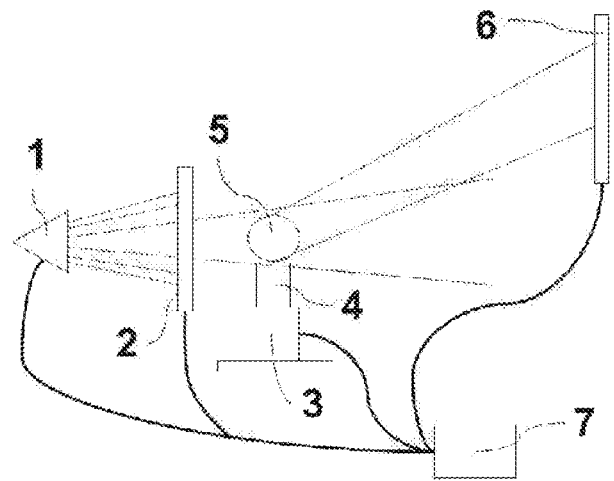

(51) Int. Cl.
| | |
|---|---|
| *G01N 23/20016* | (2018.01) |
| *G01N 23/20025* | (2018.01) |
| *G01N 23/205* | (2018.01) |
| *G01N 23/2055* | (2018.01) |
| *G01N 23/207* | (2018.01) |
| *G01N 33/38* | (2006.01) |
| *G01N 23/04* | (2018.01) |
| *G01N 23/046* | (2018.01) |
| *G01N 23/18* | (2018.01) |
| *G01N 23/201* | (2018.01) |
| *G01N 23/203* | (2006.01) |
| *G01N 23/041* | (2018.01) |

(52) U.S. Cl.
CPC ......... *G01N 23/20* (2013.01); *G01N 23/201* (2013.01); *G01N 23/203* (2013.01); *G01N 23/205* (2013.01); *G01N 23/20008* (2013.01); *G01N 23/20016* (2013.01); *G01N 23/20025* (2013.01); *G01N 23/2055* (2013.01); *G01N 33/381* (2013.01); *G01N 23/041* (2018.02)

(58) Field of Classification Search
CPC .... G01N 23/203; G01N 23/207; G01N 23/04; G01N 23/046; G01N 23/18; G01N 23/205; G01N 23/2055
USPC .................................................... 378/70–83
See application file for complete search history.

(56) References Cited

U.S. PATENT DOCUMENTS

| | | | | |
|---|---|---|---|---|
| 5,932,119 | A * | 8/1999 | Kaplan | B23K 26/032 219/121.68 |
| 6,498,829 | B1 * | 12/2002 | Borgstahl | G01N 23/20 378/73 |
| 7,136,154 | B2 * | 11/2006 | Bray | A44C 17/00 356/30 |
| 7,558,371 | B2 * | 7/2009 | Park | G01N 23/207 378/71 |
| 7,755,072 | B2 * | 7/2010 | Porat | G01N 21/87 250/221 |
| 7,796,726 | B1 * | 9/2010 | Gendreau | G01N 23/223 378/46 |
| 8,319,145 | B2 * | 11/2012 | Rosario | B23K 15/08 219/121.19 |
| 8,457,280 | B2 * | 6/2013 | Lauridsen | G01N 23/207 378/73 |
| 8,953,743 | B2 * | 2/2015 | Yasukawa | G01N 23/207 378/72 |
| 8,995,742 | B1 * | 3/2015 | Cooley | G06F 17/10 382/141 |
| 9,110,004 | B2 * | 8/2015 | Feser | G01N 23/046 |
| 9,129,715 | B2 * | 9/2015 | Adler | H01L 22/12 |
| 9,201,026 | B2 * | 12/2015 | Walls | G01N 33/2823 |
| 9,279,776 | B2 * | 3/2016 | Kleine | G01N 23/20008 |

OTHER PUBLICATIONS

Roland Diehl et al., X-Ray Fingerprinting Routine for Cut Diamonds, Gems & Gemology, vol. 40, No. 1, Spring 2004, pp. 40-57.*

* cited by examiner

METHOD OF GENERATING A FINGERPRINT FOR A GEMSTONE USING X-RAY IMAGING

FIELD OF THE INVENTION

The present invention relates to the identification of gemstones, in particular diamonds. The invention provides a method of generating a fingerprint for a gemstone that will allow gemstone and jewellery producers, traders, transporters, retailers, sellers, consumers and authorities to check the identity of a particular gemstone so that the source or rightful ownership of the gemstone can be accurately identified. Specifically, the method could be used to generate a fingerprint for any gemstone and subsequently to check the fingerprint of any gemstone against fingerprints that have previously been generated and recorded. A fingerprint generated according to the method of the present invention may have further uses, including, but not limited to, predicting the value and characteristics of gemstones that will be cut from a rough gemstone and determining the optimum way in which a rough gemstone may be cut, or distinguishing natural gemstones from artificial man-made gemstones, or detecting colour and other treatments that may have been applied to the gemstone, or further processing, visualising and presenting the fingerprint in marketing material to help consumers engage with a specific gemstone, gemstone brand or jewellery brand.

BACKGROUND TO THE INVENTION

Gemstones, particularly diamonds, can represent significant monetary or sentimental value, and any doubt or concern regarding their origin or history may affect this value negatively. In particular, concerns about illegally or unethically sourced gemstones can result in a lower retail price compared to gemstones with a proven origin. There are indications that despite established international regulations, illegally or unethically sourced gemstones regularly enter legal trade channels unnoticed. Gemstones and jewellery are also often subject to loss, theft or illegal trade, and accurately and easily identifying recovered objects, their origin or their lawful owner is a challenge.

When promoting gemstones to the end consumer, it is often challenging to effectively distinguish individual gemstones or a gemstone brand from other gemstones in a comparable category. Small physical features of the gemstone that are difficult to observe by the naked eye can have a large influence on their price. Therefore, tools that can enhance the uniqueness of gemstones can help marketing efforts.

When processing a rough gemstone, in particular a diamond, the internal flaws of the stone have a large influence on the final quality and value of the cut stone. Therefore, a map of the internal features of the stone is of great benefit to find cutting designs which maximise the value of the stone after cutting and polishing.

Gemstones are usually small in size and processed in one of a few standard cuts. This means it is very difficult to identify a single specific gemstone by simple optical means. Further, in order to obscure the identity of a gemstone it is relatively easy to re-polish, recut or irradiate the gemstone thereby changing its appearance, shape, weight and/or other physical properties. Established methods for identification are usually based on surface markings or shape of a cut stone.

Identification methods have been proposed based on detecting inclusions within a gemstone using optical means. However these methods are restricted to inclusions that provide sufficient contrast at the wavelength range of infrared, visible or ultraviolet light, and that are larger than the spatial resolution of the optical apparatus. This may not provide enough detail for unique identification of gemstones which have sub-regions of low inclusion content. Furthermore, the problem of light refraction at the outer surface of the gemstone has to be overcome, for example by immersing the gemstone in a liquid of which refractive index is matched with that of the gemstone.

The following description will focus on the issues with identifying diamonds. However, it is to be appreciated that the same issues and problems are equally applicable to any other crystalline gemstones, in particular single crystal gemstones or gemstones consisting of a small number of crystals.

Cut diamonds are classified according to the "four C's". These four C's are: carat, cut, clarity, and colour. This classification can be used as a rough identification of a specific gemstone. However, as recutting and repolishing will affect the cut and clarity of a diamond and clarity and colour are somewhat subjective judgements, this classification is of little use for identifying a specific diamond and is primarily a way of valuing a diamond.

X-ray absorption tomography can be used to map density or phase variations within the bulk of a diamond, but it may not have enough sensitivity to map thin cracks, carbon or other inclusions with similar attenuation properties to that of diamond.

In light of this problem the fingerprinting of diamonds has been proposed.

No commercially available diamond is an entirely perfect single crystal. Every diamond will have some microstructural defects including inclusions and imperfections in the crystal lattice. Imperfections in the lattice include distortions of the lattice, lattice faults, and discontinuities in the lattice. Distortions of the lattice may be described for example by an orientation, strain, or displacement field. Lattice faults include, but are not limited to, stacking faults, dislocations, and scratches. Discontinuities in the lattice may for example be due to the presence of other phases (i.e. inclusions), voids, fractures, cracks, crystal boundaries, small angle crystal boundaries, growth sector boundaries, or twinning of the crystal lattice. Distortions, faults, and discontinuities can all be located internally in the bulk of the crystal or on the crystal's surface.

The relative position and orientation of any given diamond's distortions, faults, and discontinuities will be unique to that diamond and, as such, can be considered to be a fingerprint of that diamond. A diamond's fingerprint can be used to identify and catalogue that diamond and thereby enable that diamond to be accurately and specifically identified after it has been initially fingerprinted. If the initial fingerprinting is sufficiently comprehensive and includes internal microstructural defects, rather than just surface defects, this identification should still be possible even if a diamond has been recut and/or repolished. Further, by sufficiently and accurately fingerprinting internal microstructural defects of a rough diamond it should be possible to determine whether a cut diamond was formed from that rough diamond.

As will be readily appreciated, the potential benefits of an accurate fingerprinting system that can identify and map bulk and surface microstructural defects are very significant in securing value chains, preventing illegal activities, assessing risk for insurance purposes, law enforcement, gemstone processing and marketing.

U.S. Pat. No. 4,125,770 (Lang) discloses a method of fingerprinting a diamond using images of the diamond produced using x-ray topography. These images do show some microstructural defects of the diamonds but are two-dimensional and, as such, do not show the relative three-dimensional position of each defect. Further, in order to replicate a previously taken x-ray topographic image it is necessary to take any future image with the diamond's crystal lattice in precisely the same alignment relative to the imaging apparatus.

WO98/08081 (Diehl) and the article by Diehl and Herres "X-ray fingerprinting routine for cut diamonds" (Gem and Gemology, vol. 40, Spring 2004, page 40) discloses an improved method compared to U.S. Pat. No. 4,125,770 to identify cut diamonds having an obvious unique facet (e.g. the table facet for shapes known as a brilliant cut). It requires potentially only one topography, instead of several, for the identification by eliminating the ambiguity of which symmetrically equivalent crystal lattice plane to be used. The orientation of the topograph is selected according to the crystallographic triad or diad axis closest to the current or future table facet (or another unique facet) of the stone. This implies that the gemstone must either be a cut stone, or a rough gemstone where it is already known at the time of creating the fingerprint how it will be cut, that is the future orientation of the table facet. In addition to the topograph, the orientation of the diamond's crystal lattice relative to the specific outer facet, the table facet, is determined by two polar angles and using a five circle diffractometer. As will be readily understood, the method of this document is not suitable for rough gemstones when their cut design is still unknown, or for identifying gemstones that have been recut, or for gemstones that do not have a unique facet.

CN102963153 (Zhizhong) purports to disclose a method of identifying diamonds by generating a fingerprint containing information about the internal microstructure of a diamond using polychromatic x-ray diffraction. However, this document contains little or no information as to exactly how a diamond would be positioned in order to map the microstructure and how the images would be compared. According to the disclosure of this document, when an initial map is created, a diamond is positioned and that position is recorded. No information is given about how this may be done, and what device or procedure may be used, or the aspects of crystal lattice symmetry or symmetry of the shape of cut diamonds. When a diamond is subsequently tested for matching of the fingerprint it is necessary to place the diamond in exactly the same position to achieve high resemblance of the originally created fingerprint. As the document is silent on how a diamond or the apparatus is positioned in the first instance it will be difficult, if not impossible, for the skilled person to reposition the diamond in the exact same position as to which it was initially positioned.

WO2006033102A1 (Porat) describes a system and method for three-dimensional location of inclusions in a gemstone, where a very broad range of emitters are listed and the emitter or source can optionally also be an x-ray source. However, the working principle of the proposed method is not specified, there are no references to similar prior art or the scientific literature and there are no guidelines or detailed drawings provided that would define the acquisition geometry. Many of the proposed emitter types cannot be used in the same way to implement the described method. In particular, it cannot be understood from the description whether the patent aims to utilise absorption, extinction or diffraction effects as contrast mechanism, hence the parameters cannot be chosen appropriately to implement the invention. Neither is it specified what gemstone material the method requires, for example if the gemstone can or should be crystalline. Due to the many glaring omissions from the disclosure of this document, the skilled person would understand its disclosure to be clearly insufficient and would ignore its content.

As yet, there are no state-of-the-art methods that can completely interpret the abundant information on a random crystal of origin contained in an x-ray topograph. The use of software is mentioned in the above patents as means to compare the two-dimensional topographs, however there is no disclosure about what kind of information and how is identified, extracted, processed and compared. The above inventions cannot handle diamonds that contain more than one crystal.

All methods based on two-dimensional topographs have several significant disadvantages:
1) defects from the entire volume of the crystal are superimposed which limits the amount and extent of defects they can handle;
2) they do not show the relative three-dimensional position of each defect;
3) if the diamond has been cut, the resulting pieces can only be identified in a haphazard manner;
4) considering a database with records of a large number, for example millions, of diamonds, it is unlikely that a single or a few x-ray topographs of a rough gemstone can provide both enough clarity of details and unique identification of the gemstone; and
5) the raw two-dimensional topographs cannot fully reveal the three-dimensional distribution of internal features of diamonds, and have limited value or impact when presented in marketing material.

U.S. Pat. No. 8,457,280 (Danmarks Tekniske Universitet) discloses a method of mapping the grain structure of polycrystals using x-ray diffraction contrast tomography. The disclosure of this document entirely relates to the mapping of grain structures and does not disclose how to obtain, analyse or reconstruct sub-crystal information and, as such, is not suitable for the mapping or identification of gemstones, which typically comprise a single or very small number of crystals.

The present invention solves the problem with the above disclosures in that it provides an accurate and repeatable producing of a fingerprint for a gemstone, in particular a diamond, that does not require prior knowledge about the alignment of the gemstone and that can be used to identify a gemstone consisting of very few crystals even if the gemstone has been polished, recut, or otherwise physically altered after any initial fingerprint generation.

SUMMARY OF THE INVENTION

The present invention provides a method of generating a fingerprint for a gemstone using x-ray imaging, wherein the fingerprint comprises a three-dimensional map of at least one crystal present within the gemstone including internal imperfections of the at least one crystal; the method comprising the steps of:

mounting the gemstone in a sample holder of an imaging apparatus, the imaging apparatus comprising a sample holder mounted on a sample stage, at least one x-ray source, the sample holder and the at least one x-ray source aligned along an optical axis, wherein the sample holder is movable in at least one degree of freedom relative to the at least one x-ray source and the at least one detector;

exposing the mounted gemstone to x-ray radiation from the at least one x-ray source, whilst moving the sample holder according to a search strategy that is predetermined for the gemstone based on known physical characteristics of the gemstone;

using the at least one detector to locate diffraction and/or extinction spots generated by the lattice of the at least one crystal;

utilising the located diffraction and/or extinction spots to calculate information about the position, orientation, and phase of the at least one crystal;

generating a suitable x-ray diffraction scanning strategy from the calculated information, the strategy including moving the sample holder relative to the at least one x-ray source and the at least one detector and exposing the gemstone to appropriate x-ray radiation from the at least one x-ray source as the sample holder is moved, wherein the strategy is generated to observe a sufficient number and quality of diffraction and/or extinction images for specified lattice planes of the at least one crystal to locate internal imperfections in the lattice;

scanning the gemstone according to the scanning strategy and recording the diffraction and/or extinction images using the at least one detector; and generating the fingerprint from the recorded diffraction and/or extinction images.

Within the meaning of the present invention, an internal imperfection is any feature of a gemstone's structure that is a deviation from a perfect crystal lattice structure. This includes lattice distortions, lattice faults, and discontinuities of a lattice. Lattice distortions may be due to strain acting on the lattice or any other cause apparent to a person skilled in the art. Lattice faults may be stacking faults, dislocations, scratches or any other fault apparent to a person skilled in the art. Discontinuities of the lattice may, for example, be due to the presence of other phases, inclusions, voids, fractures, cracks, crystal boundaries, small angle crystal boundaries, growth sector boundaries, twinning of the crystal lattice; internal imperfections include all of these features.

A fingerprint of a gemstone according to the present invention is at least one three-dimensional map of at least one crystal present within the gemstone including internal imperfections of the at least one crystal. The fingerprint is a three dimensional map in that it includes quantitative information about the relative location of internal imperfections in three dimensions. A fingerprint may include the location of substantially all detectable internal imperfections or it may only include internal imperfections above a specific size and/or it may only include internal imperfections within a partial volume of the at least one crystal. A fingerprint may include the location and classification of the internal defects of more than one crystal present in a gemstone. In addition to information about internal imperfections a fingerprint may include a map of surface defects of a gemstone or the location, orientation, shape, surface or volume model of crystals within the gemstone. In addition to location information about internal imperfections a fingerprint may contain further information about the internal imperfections, for example the size and/or orientation and/or type and/or shape of each imperfection.

In a simple embodiment of the invention a fingerprint may be a three dimensional map of the relative locations of a small number of easily detectable internal imperfections, for example more than five but less than ten internal imperfections. These may be the most easily detectable internal imperfections of the at least one crystal. It is anticipated, that in many cases, determining the relative location of this small number of internal imperfections will be sufficient to be a unique identifier of a gemstone.

In another embodiment of the invention, the fingerprint may be a three-dimensional reconstruction of the local diffracting power of the crystal lattice, represented and stored as a scalar field over a three-dimensional grid Preferably, a fingerprint of the present invention will not only include a three dimensional map of internal imperfections that are visible using standard optical examination but will include internal imperfections that are not detectable using standard optical examination. In particular, it is preferable that a fingerprint of the present invention includes one or more lattice fault and/or lattice distortion.

The method of the present invention is preferably used for generating fingerprints of diamonds, which will typically be a single crystal or a twinned crystal. However, it is to be understood that the method of the present invention may be used for any gemstone with a crystalline structure, whether it contains a single crystal or multiple crystals or it is polycrystalline.

In the context of the current invention, "x-ray" refers to electromagnetic radiation that contains photon energies between 1 and 1000 keV or associated photon wavelengths between 12.4 and 0.0124 Angstrom ($12.4 \times 10^{-10}$ m and $0.0124 \times 10^{-10}$ m), independent from the way it was generated. A typical applied photon energy range is, for example, between 8 and 50 keV.

The at least one x-ray source of the present invention may be any suitable x-ray source. That is, the at least one x-ray source may be any device that is capable of producing x-ray radiation suitable for imaging at least one crystal of a gemstone. This includes primary, secondary, tertiary, etc. x-ray sources. The at least one x-ray source of the present invention may include optical elements to shape the beam profile, focus, change the divergence, energy spectrum, coherence or other characteristics of an x-ray beam generated by the at least one x-ray source. X-ray sources including optical elements include, but are not restricted to: laboratory x-ray sources (including microfocus, rotating anode, and liquid jet sources), synchrotron sources (using an undulator, wiggler or bending magnet), linear accelerators, radionuclide sources, and compact light sources based on inverse Compton scattering.

In the context of the current invention, the x-ray spectrum of the at least one x-ray source refers to the x-ray spectrum of the radiation reaching the gemstone, irrelevant of whether it is a pre-selected sub-range of an originally broader spectrum emitted within the at least one x-ray source.

The effective x-ray spectrum of the apparatus refers to the combination of the x-ray spectrum of the at least one x-ray source and the detection efficiency of the at least one detector, including all elements of the at least one detector.

In respect of the present invention three types of x-ray spectra are distinguished: a polychromatic spectrum, a monochromatic spectrum and a mixed spectrum.

A polychromatic spectrum is a spectrum wherein the photons that have a sufficiently wide bandwidth of energies to potentially observe diffraction of a given (hkl) lattice plane from the entire irradiated volume of a crystal within the gemstone at a given orientation position of the gemstone and for a given beam divergence, considering Bragg's law. If the energy bandwidth of the spectrum is wide enough, diffraction from several (hkl) lattice planes can occur simultaneously. A polychromatic spectrum may be generated, for example, by Bremsstrahlung of electrons in a target material or by a bending magnet.

A monochromatic spectrum is a spectrum that is not polychromatic. A monochromatic spectrum contains photon energies in a narrow energy band, where the energy bandwidth is not sufficient to observe diffraction of a given (hkl) lattice plane from the entire irradiated volume of a crystal within the gemstone at a given orientation of the gemstone and for the given beam divergence, considering Bragg's law. For example, parts of the crystal may not satisfy Bragg's law due to the divergence of a conical x-ray beam, or the crystal lattice having local deformation (misorientation). Therefore, for this definition, the relative energy bandwidth may depend on the crystal material and the deformation in its crystal lattice, and it is typically but not necessarily between $10^{-3}$ and $10^{-5}$. In order to record the same reflection from a larger crystal volume with a monochromatic beam, the local Bragg angles may be changed over a narrow angular range by a relative movement of the source and the crystal ("rocking"). This movement, for example a rotation of the crystal, may be performed while exposing a given image or a series of images ("integration"). The reflection may be integrated in a single image (2D diffraction or extinction spot), or in several images (3D diffraction or extinction spot) where the images correspond to subsequent angular positions. The set of intensities recorded in a given area or pixel of the detector are analogous to a local rocking curve of the crystal. This integration technique is equally applicable to record an image with an x-ray energy where there is a discontinuity in a mixed spectrum.

The origin of the radiation for a monochromatic spectrum may be, for example, x-ray fluorescence from a target anode or selected from a polychromatic beam by a multilayer or crystal monochromator. It is to be understood that other photon energies, for example, higher harmonics or a lower intensity background radiation may be present in a monochromatic spectrum without significantly interfering with the detection of the nominal energy band or interfering in a predictable manner.

A mixed spectrum is a polychromatic spectrum that has at least one discontinuity, where discontinuity means a narrow distinguishable region where the intensity of the spectrum changes rapidly by photon energy (a peak or a step function) and has a much higher derivative then elsewhere, for example due to a fluorescence peak of the target anode, absorption edge of an element present in an optical element in the beam path, etc. The superposition of a monochromatic and a polychromatic spectrum is also a mixed spectrum.

A detector used in the method of the present invention may be any device capable of detecting x-ray radiation, including single pixel, 1D line, and 2D area detectors, and is not restricted to detectors with a specific working principle. In particular, detectors used in any specific embodiment of the invention may include one or more 1D or 2D spatially sensitive area detectors, with or without energy discrimination functionality. One or more detectors used in an embodiment of the invention may include solid state or flat panel detectors with direct or indirect x-ray detection, including single photon counting detectors. These have typically medium to low spatial resolution. A high spatial resolution detector may include a scintillator layer, visible or near visible light optics (such as fiber optics or microscopy objectives) and a CCD or CMOS sensor, or it may be an imaging plate with an adapted scanning or reading device. A detector may be equipped with fiber optics, collimators or lenses in order to restrict the position or direction from which x-ray beams are detected. The sensing material, sensing element and other optical elements of a detector can have a large influence on the detection efficiency of the at least one detector. Therefore, it is advantageous that the detector or detectors used in any specific method of the present invention are suitably adapted to the x-ray spectrum, spatial resolution and detection angles utilised in that embodiment.

A detector used in the method of the present invention may be an area detector. Area detectors are often produced as modules that can be assembled into a larger continuous flat or segmented or curved surface to extend the total field of view. In this patent, such assemblies are also considered to be a single area detector, whether assembled or disassembled.

The individual sensitive element of a detector is referred to as a 'pixel'. Commercially available line or area detectors typically have 100 to a few thousand pixels along one dimension, and typically an effective pixel size of 0.3 to 250 micrometers.

A detector used in an embodiment of the present invention may be an energy discriminating detector. Energy discriminating detectors measure the distribution of the detected photon energies of the radiation in specific energy bands or ranges. Energy discriminating line or area detectors measure the photon energies in each individual pixel or over the entire active area. In an energy sensitive area detector the recorded image can be represented and stored per pixel channel, for example, as a three-dimensional array or as an image stack in which each slice or image represents a measured photon energy band. Energy sensitivity is usually achieved by an electronic processing unit or by an analyser crystal.

An x-ray source or a detector used in the method of the present invention may include one or more x-ray optical elements. Any such x-ray optical element may be part of, attached to or be an independent component mounted separately from, a source or a detector and may be used to modify the energy spectrum, cross-section, intensity profile, direction, coherence, phase, divergence or any other property of the x-ray beam. X-ray optical elements that may be included in an x-ray source or detector include, but are not limited to, filters, attenuators, absorbers, apertures, slits, scintillator plates, scintillator crystals, sensor materials, analyser crystals, absorption gratings, phase gratings, monochromator crystals, condenser optics, collimators, lenses, mirrors or zone plates.

In relation to the present invention, a diffraction image is to be understood to be an electronically processed signal recorded by detecting either the presence of photons in a beam that was diffracted by the gemstone, i.e. diffraction spots, and/or the absence of photons in a direct beam that was transmitted through the gemstone (a reduction of intensity as compared to the direct beam when incident upon the gemstone) due to diffraction occurring in the gemstone, i.e. extinction spots. Extinction spots are most apparent when a monochromatic direct beam or an energy discriminating detector is used, and can be extracted by removing the background intensity of the direct beam in any manner that will be apparent to a person skilled in the art.

In some embodiments of the invention in order to optimize the detection of diffraction spots by the at least one detector, when a diffraction spot is detected by the at least one detector, the x-ray radiation generated by the at least one x-ray source may be controlled such that the area of the at least one detector detecting said diffraction spot is not directly irradiated by the at least one x-ray source but is only irradiated by the diffraction spot. This may be done using any suitable optical element. Said optical element may be integrated with or separate from the at least one x-ray source and, for example, may be one or more of an aperture, beam defining slits, a collimator, or fiber optics.

As will be readily understood, the optical axis of the apparatus of the present invention is the axis along which an x-ray beam propagates from the at least one x-ray source inside the imaging apparatus and which passes through the gemstone. An optical axis usually indicates a symmetry plane or axis of the imaging apparatus or the measurement geometry, if any. In the case of a parallel x-ray beam, the optical axis is the direction of the beam. In case of a divergent x-ray beam and a point-like source, the optical axis passes through the real or virtual x-ray source.

The method of the present invention includes the steps of scanning a gemstone according to a predetermined scanning strategy, the generation of a scanning strategy, the scanning of the gemstone using that generated scanning strategy, and the generation of a fingerprint from the results of the generated scanning strategy. Preferably these steps are controlled or carried out by a suitable processing unit. A suitable processing unit is any processing unit that is capable of receiving, processing, or controlling motor positions, recorded images and any other relevant measurable or controllable parameters, to process data in ways described hereafter, and to save or transmit said data. The processing unit will typically comprise one or more computers and it may consist of multiple independent local, distributed or remote units connected via a network. For example the processing unit can comprise computer clusters or cloud computing, and it may contain units specialised for certain computational tasks, such as graphical processing units, etc.

Preferably, the sample stage is capable of a rotation and/or translation position wherein the sample stage, the sample holder, and any gemstone mounted thereon are completely moved out of alignment with the at least one x-ray source such that a direct beam path from the at least one x-ray source can reach the at least one detector without impinging upon the stage, holder, or gemstone. This is preferable as it allows an intensity profile of the direct beam to be recorded for each scan or at regular intervals during any scan. Alternatively, depending on the stability of the imaging apparatus, such an intensity profile can also be recorded before the gemstone is mounted on, or after the gemstone is unmounted from, the sample holder. Recording the intensity profile of the direct beam is useful as reference images for normalisation of recorded diffraction, extinction or direct images with the gemstone in the direct beam. In absorption tomography, this correction is known as flat-field correction.

The imaging apparatus used in the method of the present invention may be based on an x-ray imaging system or a diffractometer. Preferred embodiments of the imaging apparatus used in the method of the present invention are as follows:

According to a first preferred embodiment the imaging apparatus may be a forward diffraction scanner. In this imaging apparatus an x-ray source and the sample stage are aligned on the optical axis. At least two of the x-ray source, sample stage and detector are mounted on a translation stage that can move along the optical axis, so that the distance between the source and a gemstone mounted on the sample stage, and the distance between the gemstone and detector can be changed. This is used to control geometric magnification, and therefore the effective field of view, spatial resolution, lattice orientation and lattice strain sensitivity. Strain and orientation sensitivity is generally better when the detector is at a larger distance from the gemstone, and strain sensitivity can be better at larger Bragg angles when a monochromatic beam or an energy resolving detector is used. However, blurring effects of a larger gemstone to detector distance have to be considered.

In a forward diffraction scanner it is preferable that the sample stage has at least three degrees of translational freedom and three degrees of rotational freedom. This may be achieved by forming the sample stage from a vertical translation stage, a base tilt stage, a rotation stage, a 2-axis translation stage and a 2-axis rotation stage. For example, the base tilt stage can be mounted on the vertical translation stage, and the rotation stage can be mounted on the base tilt stage that can tilt a rotation axis of the rotation stage towards or away from the source. The translation stage may be a two-axis sample translation stage mounted on top of the rotation stage. A two-axis rotation stage (e.g. a goniometer) may then be mounted on top of the sample translation stage. A gemstone may be mounted rigidly onto or into a sample holder which is mounted rigidly onto the sample stage. This layout of the sample stage allows for a range of {hkl} lattice planes to be brought in the diffraction condition, and to record diffraction or extinction images both with a polychromatic beam and with a monochromatic beam, and provides the integrating axis for a monochromatic beam. Furthermore it allows for performing topo-tomography (using either diffraction or extinction images) and section tomography using diffraction images. It also enables absorption or phase contrast tomography and crystallographically aligned imaging. These imaging modes will be detailed below. For extinction, absorption and phase contrast images, the source, the gemstone and the detector all have to be on the optical axis. For section topography, the detector has to be off the optical axis.

A forward diffraction scanner may have a plane of symmetry that includes the optical axis, typically this is a vertical plane. At least one of the source, sample stage or detector has a degree of translational freedom in this plane of symmetry, such that an angle between the source-to-sample and sample-to-detector vectors can be changed. This allows changing of the observable diffraction angles. The detector may be directed parallel with the optical axis or towards the gemstone and capable of detecting diffracted x-rays from the gemstone and/or x-rays from an x-ray source.

For certain methods described in this patent, the imaging apparatus is required to be configured in a way that a detector can record direct images (absorption, phase contrast or extinction images) in an x-ray beam transmitted through the gemstone. In this case, a detector must be on the optical axis.

A single detector with sufficient spatial resolution and field of view may be used to record diffraction and direct images simultaneously, or diffraction images over a wide Bragg angle range, or multiple diffraction spots. Alternatively or additionally, a single detector may be used to detect direct images and diffraction images, and changing between the two modes is performed by moving at least one of the at least one x-ray source, gemstone or the detector. In this case, an attenuator can be used over the direct beam area to decrease flux that reaches the detector in the direct beam. Optionally, direct and diffracted images may be recorded on separate detectors. Furthermore, a detector may have translational degrees of freedom to move perpendicular to a plane of symmetry or rotational degrees of freedom to change its direction. These degrees of freedom may be dependent on each other.

In addition to the stages set out above, a forward diffraction scanner used as the imaging apparatus of the method of the present invention may further comprise additional stages for alignment and calibration purposes.

A beam cross section produced by an x-ray source of a forward diffraction scanner can be shaped to be, for example, a pencil beam, conical beam, line beam, fan beam or a full parallel beam to irradiate, a line segment, a thin section or a substantial volume of the gemstone. This can be achieved in any manner apparent to a person skilled in the art.

As will readily understood by the person skilled in the art, if an x-ray source produces polarized radiation, for example if the x-ray source is a synchrotron undulator source, then the polarisation plane will be a consideration in the setup geometry. In particular, it will be necessary to be able to position the sample holder and at least one detector so that elastic scattering (diffraction) can be measured favourably.

The sample holder of the imaging apparatus of the present invention may be formed of any material that either does not significantly interfere with images detected by the at least one detector, or that interferes with the images detected by the at least one detector in a predictable way, preferably in a narrow angular range. For example, it is preferable that the sample holder is at least partially made of a material that is non- or weakly absorbing or diffracting in the relevant x-ray energy range.

Optionally, the sample holder may be formed such that a gemstone can be mounted therein and removed therefrom automatically by a robotic mechanism.

Optionally, the sample holder may be able to be mounted and orientated on the sample stage in significantly different orientations, such that by changing the orientation of the sample holder on the sample stage, the effective solid angle of projections available for creating the fingerprint is increased.

Optionally, the sample holder is mounted on the sample stage with a reproducible mechanical mount, for example a kinematical mount.

Optionally, a forward diffraction scanner may comprise more than one area detector. These area detectors may each be mounted on separate translation and/or rotation stages. The area detectors are preferably mounted in a way such that their effective coverage of diffraction angles or spatial resolution range is maximized.

Optionally, a forward diffraction scanner may further comprise a diode detector for monitoring the beam intensity generated by the at least one x-ray source. An integrating or energy discriminating diode detector may be mounted on or off the optical axis of the at least one x-ray source.

Optionally, the at least one x-ray source may be mounted on one or more translation and/or rotation stages.

Optionally, an aperture or a pair of beam defining slits is mounted between the at least one x-ray source and the gemstone, preferably close to the gemstone to provide the best defined, sharpest beam cross section and beam profile.

Preferably, the imaging apparatus has the capability to align a crystal within a gemstone for a topo-tomographic scan [Ludwig 2001] and perform a topo-tomographic scan of the crystal. This requires that a given (hkl) lattice plane is aligned normal to a physical or pseudo rotation axis of the sample stage, and the angle between the axis and the direction of a direct x-ray beam irradiating the crystal is fixed at 90 degrees minus the Bragg angle of the aligned (hkl) lattice plane, wherein the Bragg angle is determined with respect to the x-ray energy used for imaging. This can ensure that at any rotational position around the axis, diffraction can be observed from the aligned (hkl) lattice plane on the detector.

The above paragraphs detail possible features of a forward diffraction scanner. However, it is to be appreciated that a forward diffraction scanner used in the method of the present invention may comprise any combination of translation and rotation stages that allows detection of diffraction beams over an adequate solid angle, as seen from the sample holder, to allow suitable scanning of a gemstone according to the method of the present invention. The most preferable angular range to detect diffraction images with a forward diffraction scanner is about 5 to 30 degrees, but other angles may also be used.

If the beam from the at least one x-ray source is divergent at a gemstone mounted in the sample holder, geometric magnification of a projected image of a volume of the gemstone can be utilised. In simple terms, a value of the geometric magnification is defined as the ratio of the distance from the at least one x-ray source to the at least one detector (the source-to-detector distance) and the distance from the at least one x-ray source to the gemstone (the source-to-sample distance). For example, three specific variants of a forward diffraction scanner can be distinguished based on the geometric magnification they provide:

i) Very low geometric magnification or quasi-parallel beam imaging apparatus. In this apparatus the geometric magnification is close to 1. The source-to-sample distance may be large (100s or 1000s of millimeters) or the beam produced by the at least one x-ray source may be substantially parallel, achieved for example by a curved multilayer device. This apparatus generally requires a high spatial resolution detector (pixel size in the 0.5-10 µm range), it allows for a relatively large effective source size (e.g. 10s or 100s of micrometers, for example in a rotating anode) and it is less sensitive to mechanical instability. A disadvantage of such apparatus is that the effective spatial resolution and the size of the field of view cannot be controlled by changing the distances between the gemstone, the at least one source, and the at least one detector, and that the X-ray detection efficiency is usually lower at high spatial resolution. This apparatus is adapted to both polychromatic and monochromatic spectra. Synchrotron sources and beam lines are particularly suitable for use as an x-ray source of such apparatus due to the large source-to-sample distance and a low divergence beam.

ii) Low geometric magnification imaging apparatus. In this apparatus the geometric magnification is low, e.g. 1.5 to 5, and the distance between the sample holder and the at least one x-ray source and the distance between the sample holder and the at least one detector are typically in the order of 10s of millimeters. This apparatus generally requires a small effective source size (micrometers, e.g. from a microfocus source or a secondary source achieved by focusing) and a high spatial resolution detector. This apparatus allows for some limited flexibility in tuning the effective resolution and the size of the field of view by changing the distances between the at least one x-ray source, the gemstone, and the at least one detector. If a polychromatic beam is used in a low geometric imaging apparatus and an extended region of a crystal of the gemstone is irradiated at a geometric magnification close to 2, diffraction spots that are thereby generated are demagnified in the plane of diffraction, and may be deformed into a narrow band on the at least one detector, an effect known as Laue focusing. These diffraction spots carry less information about internal features of the crystal and may be utilized during alignment, in the search for reflections or for indexing reflections, with the benefit of less probability of overlap of multiple spots or overlap with the direct beam footprint, and a better signal-to-noise ratio.

iii) High geometric magnification imaging apparatus. In this apparatus the geometric magnification is in the order of 10 to 100, and a large distance between the sample holder and the at least one detector (the sample-detector distance) is used. The at least one detector has a large field of view and may have large pixels (e.g. 10 μm to 200 μm). This apparatus requires a small effective source size (micrometers). This can be achieved, for example, by using a microfocus source or by focusing. This apparatus allows for a wide range of effective resolution and field of view by changing the distances between the at least one x-ray source, the gemstone, and the at least one detector. It may be an advantageous feature of the use of this apparatus that, by decreasing the magnification, more diffraction spots can be observed by the at least one detector and used for calculating information about the position, orientation, and phase of crystals in the gemstone.

A forward diffraction scanner will generally have a single x-ray source and a single detector. However, a forward diffraction scanner used in the method of the present invention may further comprise additional x-ray sources and/or detectors in order to measure reflections simultaneously in an advantageous geometry.

For choosing parameters for a given implementation, the crystallography of the gemstone, the energy spectrum of the beam, the Bragg angles, the acquisition geometry, the source size, detector pixel size, detector energy resolution the blurring effect at the detector due to a larger source size, the extent of the crystal lattice deformation are major factors to be adjusted in order to observe the required diffraction or extinction signal. Diffraction principles are described in, for example, André Authier, Dynamical theory of X-ray diffraction, Oxford University Press, 2001 and D. K. Bowen, B. K. Tanner, High Resolution X-Ray Diffractometry and Topography, Taylor and Francis, 1998. It is to be anticipated that the skilled person would readily understand all relevant considerations and would be able to design an appropriate forward diffraction scanner.

As an example of additional detectors, a forward diffraction scanner may comprise one or more large field of view detectors in addition to a high resolution detector in order to increase the solid angle coverage of a gemstone to facilitate or speed up the steps of using the at least one detector to locate diffraction and/or extinction spots generated by the lattice of the at least one crystal and utilizing the located diffraction and/or extinction spots to calculate information about the position, orientation, and phase of the at least one crystal.

As an alternative, the imaging apparatus used in the method of the present invention may be a compact instrument. A compact instrument is a relatively compact and mechanically simple instrument that comprises a sample stage, a fixedly mounted polychromatic x-ray source, which provides an effective source size between one micrometer and 100 micrometer and a divergent beam, and a fixedly mounted high-resolution detector, which is used at a low geometric magnification. The sample stage is provided such that it is rotatable around at least two axes, and may have anywhere from 0 to 3 different degrees of translational freedom. The effective or mean Bragg angle and the geometric magnification may be changed by varying the translational position of the sample stage; if the sample stage has no degrees of translational freedom those parameters are fixed. The compact instrument can record diffraction and/or extinction images and may be capable of performing topo-tomographic scans either way. In embodiments where extinction images are recorded, the detector is preferably an energy resolving detector, and the extinction signal is extracted from the energy channel corresponding to the local Bragg angle along the beam path which strikes a given pixel. A compact instrument may be preferred for methods of the present invention that are only used to generate fingerprints for similar gemstones i.e. gemstones of the same material and of similar size. For these gemstones the use of more complicated imaging apparatus may be unnecessary.

As a further alternative the imaging apparatus used in the method of the present invention may be section topography apparatus. Such apparatus will be well-known to the person skilled in the art. Section topography apparatus generally have a single detector that is positioned off the optical axis and is oriented towards the sample stage such that it can detect diffracted beams from a gemstone at angles of approximately 30° to 90°. That is, the detector can detect diffractions having a Bragg angle between 15° and 45°. In section topography a section of a gemstone mounted in the sample holder is irradiated with a narrow monochromatic or polychromatic x-ray line beam from an x-ray source and topographs are recorded. The advantage of this geometry is that the topographs provide a direct mapping of the irradiated section of the gemstone, and by irradiating subsequent sections by translating the crystal relative to the beam internal imperfections of the gemstone can be mapped over the entire volume of the gemstone without requiring a three-dimensional reconstruction process. When using a monochromatic beam, the translation can also be used for signal integration simultaneously. A disadvantage of section topography is that the higher Bragg angles typically require lower x-ray energies from the strongly scattering lattice planes, and absorption may restrict the size of a crystal that can be mapped within a gemstone.

As an alternative, the imaging apparatus used in the method of the present invention may be an x-ray tomography apparatus that records extinction images in the direct x-ray beam, and no diffraction images. In such apparatus the at least one x-ray source, the gemstone and the at least one detector are mounted on the optical axis. The geometric magnification may be either fixed, or may be able to be changed by changing the position of at least one of the at least one x-ray source, at least one detector and the gemstone. The sample stage may be a rotation axis perpendicular to the direction of the direct x-ray beam. The apparatus can record both extinction and absorption, and optionally phase contrast images. In a preferred tomography apparatus a parallel monochromatic beam or a narrow relative energy bandwidth x-ray beam is used. Indexing of the crystals within the gemstone can be performed based on the extinction images. During a scan using a tomography apparatus a gemstone is rotated, for example, through 90 degrees or 180 degrees or 360 degrees and images are recorded at fixed angles or integrated over small angular intervals which provide projections of approximately even angular coverage of the gemstone.

As a further alternative the imaging apparatus used in the method of the present invention may be a four-circle or kappa diffractometer equipped with an area detector.

When carrying out the method of the present invention a gemstone is mounted rigidly to the sample holder mounted on a sample stage. This may be done manually or automatically by a robot. The gemstone does not have to be aligned precisely, although some approximate pre-alignment for specific shapes of gemstones may be realised mechanically by the sample holder or the sample stage.

The gemstone mounted in the sample holder may be mounted in a piece of jewellery. In such cases, the gemstone must be mounted in the sample holder such that at least a sub-volume of the gemstone can be imaged using the imaging apparatus.

Polished facets of gemstones (such as the table facet of a brilliant cut) are often orientated approximately parallel to a given crystallographic plane. This relation can be used to find the crystallographic alignment faster on cut stones.

For logistics, transportation and security aspects it may be advantegeous to be able to generate or check the fingerprint of a gemstone that is within a closed container. This can be possible if a suitable container is used. A suitable container may be partially transparent to allow visual inspection of a gemstone or may be opaque for security or structural purposes. A suitable container has to be constructed in a way that the enclosed gemstone can be imaged with the required x-ray beam spectrum and geometry. In particular, at least some parts of the walls of the container have to be sufficiently thin and transparent to x-rays such that absorption and attenuation by the walls is limited, for example to 80%. Background noise in images from x-ray scattering and fluorescence emission by the container is preferably also kept to a minimum. In general, preferred materials from which to form a suitable container comprise elements with low atomic number and have high mechanical strength and/or stiffness, for example aluminium, magnesium or titanium alloys, polymers, glass or carbon fiber reinforced composites. In case of crystalline materials, single crystals or a fine grain structure is preferred to avoid strong, unpredictable diffraction contribution in the images from the container. A cylinder or other simple geometric shape is preferred for a constant or predictable attenuation effect in the images.

It is assumed that following the mounting in the sample holder the crystallographic orientation of the gemstone is not aligned relative to the imaging apparatus. Depending on the effective solid angle covered by the field of view of the at least one detector, and the monochromaticity of the beam from the at least one x-ray source, it is not certain that diffraction will occur in the initial orientation and diffraction or extinction spots may not be detected by the at least one detector in this orientation. Known methods in crystallography can be used and adapted to align a crystal lattice on an instrument using diffraction signals. Some additional guidelines are given in the following.

The gemstone is exposed to x-ray radiation whilst moving the sample holder according to a predetermined search strategy. That is, images are recorded by the at least one detector at various gemstone positions (orientation and optional translation) in search of diffraction or extinction spots. This search is carried out according to a predetermined search strategy, which can be optimised for certain crystal structures and materials. The predetermined search strategy is devised based upon technical considerations including, but not limited to, the geometry of the apparatus, the beam divergence, the effective x-ray spectrum, the detector position and characteristics. The predicted search strategy may also be optimized based upon the expected crystal structure of the gemstone and its symmetry. For example, if the gemstone is known to be a diamond then the (hkl) Miller indices of the expected observable lattice planes will be known. From these parameters the angular range of the gemstone that is required to be imaged in order to cover a minimum number of reflections can be predicted and thereby a search strategy can be predetermined.

The predetermined search strategy comprises a series of relative positions of the at least one x-ray source, the sample holder, and the at least one detector, and acquisition parameters (e.g. acquisition time and x-ray spectrum) to use to locate diffraction and/or extinction spots. Advantageously, the images recorded and processed during the predetermined search may be used as active feedback to adapt the search. For example, after the detection of a plurality of diffraction spots it may be possible to more accurately predict the location of further diffraction spots and the search may be adjusted accordingly.

The location of as few as 3 or 4 diffraction and/or extinction spots per crystal may be sufficient to determine the orientation and position of a crystal in a gemstone. However, it may be preferable that between 5 and 50 diffraction and/or extinction spots are located for accuracy and robustness.

A simple predetermined search strategy according to the present invention is to rotate the gemstone around an axis perpendicular to the optical axis, recording images using the at least one detector at fixed angular intervals, and analysing the recorded images for changes in measured x-ray intensity.

As will be readily appreciated, the number of diffraction and/or extinction spots located using the predetermined search strategy should be sufficient to either confirm that the gemstone is a single crystal or to perform indexing of the contained crystals of interest of the gemstone. Diffraction or extinction spots that are located but that are below a certain size or show a large mosaic (angular) spread due to lattice imperfections or do not meet some other predefined criterion may be neglected at this stage.

The use of a polychromatic x-ray beam may allow for more efficient and faster search for diffraction and/or extinction spots as compared to a monochromatic x-ray beam. In a preferred embodiment of the invention, the at least one x-ray source allows changing between monochromatic and polychromatic beam, for example, by using a plurality of different x-ray sources or by moving a monochromator unit into the direct beam path of a polychromatic x-ray source upstream from the gemstone.

In methods of the present invention using an imaging apparatus wherein the at least one x-ray source is a polychromatic x-ray source and the at least one detector is a large field of view detector (as discussed above), a single image or only a few images may be required to record sufficient diffraction spots to determine the position, orientation, and crystallographic phase of crystals in the gemstone.

In methods of the present invention using imaging apparatus wherein the field of view of the at least one detector is comparable to the size of the gemstone, diffraction spots are likely to extend beyond it. In these methods the search process may involve manipulating the gemstone in such a way that a larger fraction of such a spot is detected.

The calculation of the position, orientation and phase of the at least one crystal is based on coordinates extracted from the intensity distribution of the located diffraction and/or extinction spots, such as their center of mass position.

As will be readily understood, the facets of a raw or polished gemstone, particularly diamonds, often have a specific orientation relation relative to the crystal lattice of the gemstone. While this can be utilized to help alignment or orientation determination, the crystal lattice orientation can be determined or manipulated more accurately by using diffraction or extinction.

If the gemstone is cut, the orientation of its flat facets can be measured from absorption, extinction or diffraction images or a surface reconstruction created from those images, and used to approximate a set of probable crystallographic orientations relative to the flat facets to facilitate the search for diffraction and/or extinction spots. Alternatively, the orientation of facets of a gemstone can be predefined by utilising a mechanically defined sample holder, in which the sample holder contains at least one flat plane, to which one or more facets of a gemstone can be aligned when the gemstone is mounted therein. Such a sample holder may accommodate gemstones of a specific size range and shape or cut. However, it will be understood that using the surface facets of a gemstone may not provide enough orientation accuracy to observe an expected diffraction or extinction spot, and further search may be required, especially when using a monochromatic x-ray beam.

All the above aspects may be taken into account in a predetermined search strategy.

In the method of the present invention the diffraction and/or extinction spots located during the predetermined search are utilised to calculate information about the position, orientation, and phase of the at least one crystal. This is done in the following manner.

The position and any necessary metadata (size, area, intensity, etc) of each of the detected diffraction and extinction spots are determined. The spots contain a combination of position information about the crystal of origin and direction information about the diffracting plane. Typically, spatial information of a spot is more accurate from a high spatial resolution detector (small pixel sizes), and angular or direction information of a diffraction spot is more accurate from a detector that is at a larger distance from the gemstone.

While a diffraction spot defines a corresponding plane normal (scattering vector) direction for a given position within the gemstone, an extinction spot does not define a specific plane normal direction. Knowing the geometry of the apparatus, the motor positions and the detector coordinates of the observed diffraction and extinction spots, the position coordinates can be expressed in a reference frame either fixed to the apparatus or to the gemstone.

Individual crystals are found within the gemstone and their position, orientation and crystallographic phase is calculated from the observed diffraction or extinction spots in a process usually known as indexing. Position at this stage usually refers to the center of mass position of the crystal or the spots. Indexing is performed by the analysis of combinations of reflections in a random or systematic manner and evaluating their coordinates and metadata against spatial and/or crystallographic and/or confidence consistency criteria. The consistency criteria are based on a theoretical diffraction model accounting for the apparatus and the crystal materials, and they define what is an acceptable combination of reflections that may originate from the same crystal. Spatial criterion is typically a maximum allowed distance between beam paths. Crystallographic criteria often define angles between given (hkl) lattice planes and the number of occurrences and intensity of a given (hkl) reflection. Confidence, probability or completeness criteria describe a minimum acceptable quality of the indexing of a crystal or a set of crystals and is usually quantified by comparing the observed reflections to the theoretically predicted reflections from the indexed crystals. The criteria should also account for the accuracy of the apparatus, including any potential errors in the measurements. The position, orientation and phase of the potential crystal is determined for each accepted combination of reflections.

Indexing can be performed in a simple way by systematically testing all reasonable combinations of reflections against the consistency criteria and accepting those crystals which have the highest confidence metric as solutions. Similarly, all reasonable combinations of potential crystal location and orientation can be tested systematically or randomly, and combinations with the highest confidence metric are accepted as the solution.

Indexing procedures known in 3D X-Ray Diffraction and Diffraction Contrast Tomography methods can be applied. It is considered that, based on this description and their common general knowledge, the skilled person would readily understand how to index a gemstone from the detected diffraction and/or extinction spots.

There are a number of different ways to perform indexing of a gemstone. An indexing algorithm has to account for the x-ray spectrum and the divergence (local beam directions) of the x-ray beam. It is possible to use spatial criteria only without knowledge of the crystal structure of the gemstone to locate potential crystal positions within the gemstone. For example, an extinction spot indicates a crystal position along the direct beam path crossing the center of the spot, and the crystal position can be found as the intersection of lines from an adequate set of extinction spots. In another example, when using diffraction spots only and the same reflections are detected multiple times, for example a Friedel pair of (hkl) and (-h-k-l) reflections, the crystal position and the diffracting plane normals can be determined using spatial criteria only. The crystallographic phase of the crystal, the (hkl) indices of the observed reflections, and potentially a refined position and orientation of the crystal can be found in a second step, wherein crystallographic criteria are applied knowing the possible positions of the crystals at least approximately.

Examples of indexing algorithms that apply only crystallographic criteria or a combination of spatial and crystallographic criteria can be found, in: S. Schmidt; GrainSpotter: a fast and robust polycrystalline indexing algorithm; J. Appl. Cryst. (2014). 47, 276-284; Peter Reischig, Andrew King, Laura Nervo, Nicola Vigano, Yoann Guilhem, Willem Jan Palenstijn, K. Joost Batenburg, Michael Preuss and Wolfgang Ludwig; Advances in X-ray diffraction contrast tomography: flexibility in the setup geometry and application to multiphase materials; J. Appl. Cryst. (2013). 46, 297-311; and U.S. Pat. No. 8,457,280 B2.

In many embodiments of the method of the present invention the gemstone may comprise only one or a few crystals. In these cases the number of observed diffraction and/or extinction spots is small, and indexing is not computationally challenging. Nevertheless, indexing algorithms have been demonstrated to handle hundreds or thousands of crystals and, as such, the method of the present invention is also applicable to gemstones containing large numbers of crystals.

An alternative way of applying spatial and crystallographic criteria is to discretise the volume of the gemstone and the crystal orientation space, and simulate the observed diffraction or extinction spot positions for each position and orientation combination in a random or systematic manner. For an example, see [Li 2013]. The phase, orientation, position and shape of the crystals is found by finding the combinations with the highest confidence metric. This is usually a computation intensive task, and algorithms may apply Monte Carlo methods.

As an optional initial step before indexing, it can be established whether the gemstone is a single crystal or it consists of multiple crystals by comparing the number, position and metadata of the recorded diffraction and/or extinction spots to simulated parameters. For example, a simple assessment on the number of crystals can be based on the number of reflections or their clustering according to size or intensity. The determined number of crystals may be used as an input for the indexing, thereby simplifying the indexing.

The crystallographic phase of any crystal is either determined from a list of possible known candidates typical for the given gemstone or it is established in a yes/no manner whether or not the crystal is of the same crystallographic material as the gemstone. The lattice parameters and the crystal structure (crystallographic spacegroup) of the list of possible phases are known for most gemstone materials. Some specific variants of a crystal can be identified at this stage, such as a single or twin crystal, polycrystal, etc. In some embodiments of the invention a polycrystal gemstone can be rejected for further investigation at this stage.

The crystallographic phase of the crystals is either determined during the indexing process by enforcing crystallographic criteria describing the possible list of phases, or it is determined in an additional step. If it is determined after the indexing, the Bragg angles associated with the observed diffraction or extinction spots can be computed from the crystal position and the orientation of the diffracting lattice plane, and the angles between observed lattice planes can be checked against the theoretical crystal structures in the list of candidates. The lattice spacings of the various (hkl) planes can be computed from Bragg's law when the wavelengths of the diffracted x-rays are known, for example, when a monochromatic beam or an energy resolving detector is used. If a polychromatic beam is used with a detector that is not energy sensitive, the x-ray wavelength of the recorded reflections are not measured explicitly. If the scattering vectors of the reflections are measured to a high angular precision, the shape of the crystal unit cell can be computed, and it is only a scalar scaling factor (the size of the unit cell) that may be unknown. Knowing the effective x-ray energy spectrum of the apparatus, this scaling factor and thus all lattice parameters can be found by fitting the simulated and observed intensities of the reflections of a crystal, using regular fitting algorithms. The accuracy of the found scaling factor is low in case of a few reflections, but improves with a larger number of reflections. Using a set of different beam energy spectra and recording reflections for each, for example by applying different acceleration voltage in the source, the number of reflections in the fitting can be increased. These methods can therefore be used to distinguish or refine both the shape and the size or scaling of the crystal unit cell. Hence, crystallographic phases with the same crystal structure of which unit cells only differ in a scaling factor, for example two different cubic crystals, can potentially also be distinguished. Fitting of the intensities may provide less precision in the lattice parameters compared to cases where the wavelengths are known. Preferably, the required precision is such that the potential relevant phases can be distinguished.

The steps of locating diffraction and/or extinction spots and the indexing processes can be combined or applied iteratively for simplicity, efficiency or speed. After an indexing process, the motor positions of the source, detector and the sample stage required to observe a given (hkl) diffraction and/or extinction spot can be computed.

Within the scope of this invention is a method wherein the step of locating the diffraction and/or extinction spots and the subsequent step of scanning the gemstone according to the scanning strategy are carried out in separate imaging apparatus. As will be readily appreciated, the necessary orientation of the gemstone in the imaging apparatus in which the step of scanning the gemstone according to the scanning strategy is performed may be determined from the step of locating the diffraction and/or extinction spots and the calculate information about the position, orientation, and phase of the at least one crystal.

A suitable x-ray diffraction scanning strategy according to the present invention includes necessary requirements of the scan and a sequence of commands for execution of the scan. The scanning strategy is generated in such a way that a sufficient number of sufficiently detailed diffraction, extinction, absorption or phase contrast images are recorded from the crystals of interest in order to generate a fingerprint for those crystals. A sufficient set of images is defined by a minimum number of images observed from specified {hkl} families reflections, and an angular coverage of the projections of the gemstone volume provided by those images.

As explained later, in addition or as an alternative to generating a fingerprint, the scanning strategy may record sufficient images to generate a three-dimensional map of crystal boundaries, lattice defects and inclusions in the crystals to optimise cutting of the gemstone and/or to generate one or more two-dimensional unique identifying maps of the gemstone.

The best scanning strategy for a given gemstone material, size range and purpose may be determined experimentally by statistical analysis of data from a suitable set of gemstones. Alternatively or additionally, the best scanning strategy may be determined theoretically.

The generated scan may be carried out according to an execution sequence. This execution sequence may be generated by an algorithm that computes acquisition parameters including, but not limited to, motor positions, energy spectrum, exposure time, beam cross-sections and focusing. The acquisition parameters of the execution sequence will be those required for observing a sufficient set of diffraction images for predefined (hkl) lattice planes of all crystals of interest. Certain reflections of more than one crystal may overlap with each other, such reflections may be omitted from the generated scan. Motor positions may be computed in a way that the detector area is efficiently used. An optimised execution sequence is preferably generated using an algorithm that takes into account at least some aspects of the instrument geometry, available beam cross-sections, focusing capabilities, the motion ranges of the sample stage, effective energy spectrum of the apparatus, crystal structure, Bragg angles, estimated crystal size, detection and overall scanning efficiency, available scanning time, the type of reconstruction, the purpose of the scan, extent, range or type of deformations of the lattice, defect or feature density in the crystal, surface damage or surface contamination on the gemstone, other externally supplied information (for example shape information from absorption tomography) as well as any other relevant considerations.

In case of low feature or defect density as few as two projections may be sufficient to locate and characterise each feature in three dimensions and thereby generate a comprehensive fingerprint. For a better definition and higher reliability, more projections are preferred. For a highly detailed fingerprint (for example when the defect density is high) or for misorientation or strain field reconstructions, the number of projections (images) may be required to be higher, in the order of tens, hundreds or thousands.

The generating scanning strategy can include recording the same reflection at several angular positions over a wide angular range that provide significantly different projections from which a three-dimensional reconstruction of a crystal volume can be created.

In a preferred embodiment of the invention, the scanning strategy includes a topo-tomographic scan, wherein a (hkl) lattice planes of a crystal is aligned perpendicular to an axis of rotation. Furthermore, the axis of rotation is aligned at an angle to the direct beam where the angle is 90° minus the Bragg angle of the (hkl) lattice plane. The gemstone is rotated around the axis and images are recorded at predefined angular intervals. The axis of rotation is preferably provided by a single rotation stage to minimise mechanical errors. In case of such an alignment, the extinction or diffraction spots of the (hkl) lattice plane can be observed on the same detector area at all rotational angles. This is called a topo-tomography alignment, and will be well known to the person skilled in the art. When a monochromatic beam is used, the alignment and the Bragg angle has to be maintained accurately during the rotation, and it may involve integrating the images over a small angular interval by rotating the crystal around a second axis sufficiently perpendicular to the first axis of rotation. When a polychromatic beam is used, the alignment requirement is much less strict, since the Bragg angle can change over a wide range corresponding to the x-ray energy and wavelength spectrum. Displacements of the diffraction spot on the detector during the rotation can be accounted for in the reconstruction, knowing the crystal alignment and the projection geometry. Using such an alignment, a large angular coverage can be achieved and an entire three-dimensional reconstruction can be obtained from a single (hkl) reflection.

The topo-tomographic scanning geometry described above can be implemented using any embodiment of the imaging apparatus that provides the required degrees of freedom.

In the generated scanning strategy a (hkl) plane and a crystal orientation may be selected such that more than one diffraction spot is recorded simultaneously on the at least one detector or on different detectors.

The generated scanning strategy is preferably created such that required and observable (hkl) reflections with the highest signal-to-noise ratio are preferred for the scan, and the angular coverage as seen from the gemstone is optimised for the purpose of generating the fingerprint.

Optionally, the generated scanning strategy may include imaging the gemstone to produce tomographic images and/or surface reconstructions of the gemstone in order to provide further information about the external and internal features of the gemstone.

According to the method of the present invention, the gemstone is scanned according to the generated scanning strategy. In particular, the sample stage, the at least one x-ray source and the at least one detector are controlled appropriately to carry out the scan. For example, the components of the imaging apparatus may be moved using motors of the imaging apparatus and potentially other acquisition parameters are changed to bring a given lattice plane of a given crystal into diffraction on a given detector wherein the image or set of images are recorded. This is repeated for each step in the scanning strategy, and the projections and their corresponding imaging parameters are processed and digitally stored.

The fingerprint may be generated during or after the scan, depending on the specific algorithm that is used. Pre-processing can be carried out immediately after an image has been recorded. Optionally, the generated scanning strategy may be updated by a feedback loop from the (ongoing) generation of the fingerprint, and the list of reflections and orientations to be scanned can also be updated.

The orientation of the crystal lattice relative to the generation of the fingerprint, a crystallographic spacegroup and lattice parameters may also be recorded as part of the fingerprint. Preferably, a fingerprint is made in the reference frame of a crystal, wherein coordinate axes of the fingerprint correspond to the crystallographic axes of the crystal. This enables finding the orientation of the fingerprint easier and faster by applying the symmetry operators of the given crystal system.

Any diffraction image, including extinction spots or diffraction spots or a combination of both can be used to generate a fingerprint.

The generation and any subsequent reading of a fingerprint can be done by any of the apparatus or method described above. A reading device may be different from the imaging device used to generate the fingerprint, e.g. it may be designed to be a more simple or economic implementation, restricted to certain types and sizes of gemstones or identification mode, and it may use a different scanning strategy from the one used in the imaging apparatus used to generate the fingerprint. Rather than repeating the procedure used for generating a fingerprint, a reading device and the method of reading the fingerprint of the gemstone may be optimised for satisfactory identification while minimising the requirements for the scan, including scanning time. For example, the analysed volume, number of lattice planes, accuracy, defect types, etc. can be limited as compared to initial fingerprint generation. The scanning strategy for the reading can be updated continuously during the reading scan according to the data being recorded. Nevertheless, it will be understood that the reading of a fingerprint of a gemstone for which a fingerprint has previously been generated will generally comprise all of the steps of claim 1 of the present invention.

During the reading of a gemstone that has previously been fingerprinted according to the method of the present invention, diffraction and/or extinction images may be recorded to partially or entirely generate a new fingerprint of the gemstone, preferably in the reference frame defined by crystallographic axes of a crystal lattice of the gemstone. Despite this, it is likely that there will be a rotational and translational offset in the relative position of the new fingerprint and the original fingerprint, generally of three degrees of freedom in each. The symmetry of the crystal lattice determines how many crystallographically equivalent orientation positions the crystal lattice can have, and only one of those coincides with the orientation position used for recording the original fingerprint. Therefore, to restrict the range of possible orientations and help find a match when compared with the original fingerprint, the new fingerprint may be transformed into each of the reference frames of the equivalent orientations. For such coordinate transformations the symmetry operators of the crystal lattice are used. The higher the symmetry, the more equivalent orientations there are. For example, diamond has a cubic crystal lattice for which the number of equivalent orientations is 24.

In some embodiments of the present invention the orientation used for creating the original fingerprint may be defined more specifically relative to a surface or volume model or flat facets of the gemstone, and this definition can be used to find the same orientation equivalent during identification, provided that the surface or volume (shape) of the gemstone has not been changed significantly since the recording. Depending on the shape and the symmetries of the surface (symmetry of the cut), the number of equivalent orientations can be reduced to a single orientation, in which case the translational uncertainty in the relative position of the new and the original fingerprint also diminishes. However, in order to avoid misidentification if a gemstone is cut or polished subsequent to initial fingerprinting it may be necessary to subject a new fingerprint that does not match any previous fingerprint to coordinate transformations in the manner set out above. This may only be necessary if the new fingerprint does not match a previous fingerprint.

Any coordinate system can be used for recording, storing or comparing fingerprints but the aspects of crystal symmetry will apply in all cases.

It is readily understood from the scope of this invention, that the fingerprint of a gemstone may be changed over time, for example by cutting the gemstone, and that the identification may be performed based on partial fingerprints. Fingerprints may be compared, for example, in one of the following three identification modes:

1) Identity Verification:

Confirming/verifying whether the inspected gemstone is the same, or used to be part of a given gemstone previously added to a database. This requires comparison with one given existing fingerprint in the database, which is chosen based on an identification number, name, index, tag, etc. that is known for the gemstone to be inspected. Alternatively, the scanning strategy can be defined in a way that it identifies a relatively short list of key features/defects sufficient for verification at a certain confidence level.

2) Identity Search:

Searching a database for potentially existing records of the gemstone to be identified. This, in principle, requires comparing with or checking against all existing records, and may be a computationally intensive process.

3) Matching:

Fingerprints of two or more gemstones are compared to each other and potentially to other records in the database to determine whether the gemstones may originate or had been part of the same gemstone before they were separated, or to determine if they are related in any other ways.

Furthermore, the nature and distribution of features in the fingerprint can be used in determining the possible geographical origin of a natural gemstone or to detect artificial, man-made gemstones. Certain growth patterns are known to be indicative of artificial production processes (for example diamonds made by a CVD or HPHT process).

The fingerprints may also be used in any other manner or for any other means that are apparent to a person skilled in the art.

To compare two or more fingerprints adapted algorithms may be used that perform the comparison in two steps:

1) Exclusion:

Records are excluded to be a potential match based on additional information to the fingerprint, for example, dimensions, volume, carat, cut, clarity, color, dates and places related to the processing history of the gemstone. Furthermore, classification and an index of the type, size, spatial distribution and statistics of identified defects or features in the fingerprint. The surface or volume model, facet angles and their relation to the crystal lattice can be used for cut and polished gemstones. This exclusion step can be a computationally simple and fast procedure, it may primarily use relational operators and may be typically implemented using a database management system, with the aim to limit the number of candidate fingerprints that remain to be correlated in the following step.

2) Fingerprint Correlation:

One or more three dimensional reconstructions in two fingerprints are compared/correlated. When the three dimensional reconstruction is a list of lattice features or defects, the algorithm may perform a random or systematic search over some or all listed lattice features or defects. When the three dimensional reconstruction is a volume represented by a three dimensional array, operations may be performed on a sub-set or all elements (voxel) of the arrays. If the gemstone has been cut since the original fingerprint was recorded, the new fingerprint will be smaller and a subset or sub-volume of the original fingerprint. An algorithm may find the uncertainty in the relative orientation and position between fingerprints by an optimisation step which minimises the differences between the two fingerprints; this may be an iterative algorithm. The possibilities in orientation offset can be restricted by the crystal symmetry, as explained above. Comparing two surfaces or volume models, if they exist and form part of the fingerprints, and assuring sufficient overlap of the two can restrict the position offset range and the subset or sub-volume of the original fingerprint to be searched and compared. Any adapted algorithm known in the field of signal and image processing, optimisation or multivariate statistics can be used, for example, image registration methods, optical flow, cross-correlation, linear and non-linear least square minimisation, pattern recognition, cluster analysis, principal component analysis. The correlation algorithm computes a confidence metric (a number or a set of numbers) based on which the matching of two fingerprints can be established or excluded automatically or by the user. Measured images, reconstructions or other relevant information can also be presented to the user to help the identification/comparison.

Although the creation of a three-dimensional map of lattice faults (i.e. a fingerprint) is technically more challenging, more time consuming and requires more computation power, it provides a more distinctive and more robust fingerprint and therefore higher reliability than a set of two-dimensional images, as disclosed in the prior art.

Benefits of the fingerprints of the present invention over two-dimensional images include the following:

1) The three-dimensional approach, spatial consistency/redundancy and digital processing enables suppressing the noise, background, artifacts and less relevant features in the fingerprint; this may include physical/mathematical modeling of the observed images;
2) Features do not overlap, hence are more distinguishable in three dimensions than in two, even at high defect densities;
3) Once a fingerprint has been created, it can be made independent from the scanning method, apparatus and acquisition parameters; and
4) Rendering and visualization of the three-dimensional fingerprint in images or a movie provides a better, more detailed, more unique, more compelling, more engaging view of the internal structure of a gemstone.

These aspects improve the robustness, reliability and in certain cases the speed of (automatic) identification or comparison.

Adding a surface or volume model of the gemstone to a fingerprint helps but is not essential for the identification.

If the volume, shape, dimensions, facet angles, etc. of a gemstone has been changed, for example by cutting or polishing, since a fingerprint of that gemstone was created, the unchanged sub-region of the 3D fingerprint can still be used for reliable automated identification.

A fingerprint can be created, stored and compared in various formats, for example a binary, discrete, integer or floating point volume representation or a list of features or defects with their three-dimensional coordinates, dimensions and possibly other properties.

Points of reference can be identified within or on the surface of a gemstone that are visible to the naked eye or via a microscope or magnifying glass or other optical device to help visual inspection of the gemstone and its internal features. The position, orientation and nature of features in a fingerprint may be described relative to the points of reference via text, figures, photographs, animation or other visual means. This information may be added to a fingerprint and presented to a user or customer, etc.

Lattice imperfections create contrast in the diffraction and/or extinction images due to locally varying diffracted beam intensity and direction, phase interactions, absorption, extinction, refraction and possibly other effects. The influence of these effects on the images depends on the local properties of the gemstone material and the components and layout of the imaging apparatus. Applicable diffraction models often only described a simplified case and neglect or approximate several effects. For reconstruction and images filtering purposes in the current invention, typically two types of models are preferred:

1) Comprehensive models exist to describe x-ray topographs from various types of isolated defects and defect clusters in an ideal crystal, accounting for phase interactions using, for example, Kato's eikonal theorem or Takagi's theorem. For a detailed description of such models, see Authier, André: Dynamical theory of X-ray diffraction. IUCr monographs on crystallography, no. 11. Oxford University Press (1st edition 2001/2nd edition 2003). ISBN 0-19-852892-2 and Juergen Haertwig; Hierarchy of dynamical theories of x-ray diffraction for deformed and perfect crystals; J. Phys. D: Appl. Phys. 34 (2001) A70-A77. These models are most useful to operate at the level of dislocations on the nanometer or micrometer scale. In the current invention, they may be used to create image or volume filters for certain types of defects or defect clusters, for example dislocations or dislocation densities.

2) Another relevant type of models describes orientation fields within deformed crystals at the micrometer to millimeter scale, usually neglecting phase interactions, and using elements of the kinematical diffraction theorem see S. F. Li and R. M. Suter; J. Appl. Cryst. (2013). 46, 512-524; Adaptive reconstruction method for three-dimensional orientation imaging, and H. H. Liu, S. Schmidt, H. F. Poulsen, A. Godfrey, Z. Q. Liu, J. A. Sharon, X. Huang; Three-Dimensional Orientation Mapping in the Transmission Electron Microscope; Science 13 May 2011: Vol. 332 no. 6031 pp. 833-834. For the current invention this kind of model is preferred to describe a deformation field within a crystal.

In certain cases, however, for example to locate cracks within the volume, detailed physical models may not be required. Instead simple geometric principles can be used.

In the current context two types of lattice features or defects may be distinguished:

1) local defects: for example, individual dislocations, stacking faults, inclusions which cause localised, distinguishable contrast in the image;
2) long range defects: a deformation, misorientation or strain field or defect densities or distributions that are analysed or quantified over a sub-region or the entire volume of the crystal Various types of characteristics or parameters can be reconstructed and form part of a fingerprint of the present invention, depending on the gemstone material and the imaging apparatus used, for example:

1) Direct gray scale reconstruction: projections are not analysed for the presence of defects, and a gray scale reconstruction is based directly on the measured intensities. The reconstructed property can be seen as local effective diffracting power of the crystal.
2) Unclassified local defects: projections or reconstructions are analysed for contrast features with consistent size, shape and location, but the type or nature of the defects is not analysed.
3) Classified local defects: projections or reconstructions are analysed to find certain known types of lattice defects, for example dislocations or inclusions. The contrast they produce is identifiable, recognisable.
4) Local defect statistics: local feature or defect density, frequency, orientation, morphology, correlation or other local statistical parameters that describe a clusters of defects are reconstructed.
5) Deformation field: the fingerprint includes a reconstruction of three-dimensional displacement, orientation or strain field. In particular, the local orientation or misorientation can be described with 3 components in a chosen crystal orientation representation, the local strain state can be described with 6 components of a strain tensor (or 5 deviatoric strain components), and deformation can be described with 9 components of the deformation or displacement gradient tensor. These types of reconstructions are detailed below.

A fingerprint according to the present invention will include information on at least one, or optionally all indexed and scanned crystal or sub-crystal of a gemstone.

In a preferred method of the present invention a fingerprint may comprise a quantitative reconstruction of a three-dimensional deformation field of a crystal lattice within a gemstone from diffraction or extinction images. This may be performed by using iterative algorithms and an adapted physical model. Local crystal orientation and strain components relative to a reference state can be treated as unknown variables in the reconstruction. They may then be determined or refined potentially together with other local variables related to density, crystallinity or diffracting power that can be used to describe the shape of a crystal, as they are close to zero where there is no crystal material. A crystal volume may be represented on a grid and the resulting model will share characteristics of ray tracing and finite element methods.

When optics that define or restrict the direction of the x-ray beam that is detected or passes through an optical element is used for imaging, the orientation reconstruction problem can be simplified. For example, when a collimator or lens with small angular acceptance is used as part of a detector, the detected beam direction, and thus possibly the diffracting plane normal directions, can be known.

There are a number of line-shaped, planar or directional internal features (or imperfections) of crystals that tend to align with certain planes of the crystal lattice, for example growth bands, microcracks, inclusions, and precipitates. The contrast of such features in the diffraction or extinction images can be improved by aligning them parallel to the diffracted or transmitted beams, so that their contrast is concentrated over a smaller area on the detector (in less pixels). In this case, attenuation or phase contrast from features along the beam direction may also contribute to the observable contrast.

In light of the above, the contrast effects to enhance directional features can be maximised by aligning the (hkl) lattice plane along which line-shaped or planar features are expected to be present parallel to the diffracted x-ray beam, when recording diffraction images, and parallel to the transmitted beam, when extinction images are recorded. In case of a divergent beam, this alignment may not be accurately satisfied for the entire crystal volume.

According to the present invention a fingerprint of the present invention is a three-dimensional map of at least one crystal present within the gemstone including internal imperfections in the crystal. A fingerprint may additionally include two-dimensional diffraction images of the gemstone, such as those disclosed in U.S. Pat. No. 4,125,770. The fingerprint can be generated using diffraction and/or extinction images in any manner set out above or that would be apparent to a person skilled in the art.

The orientation and position of the fingerprint according to the present invention may be defined relative to a coordinated three-dimensional model/reconstruction/representation of the outer surface or the volume of the gemstone. The surface or volume model is a true three-dimensional representation of the gemstone which allows for computing any dimension, distance, angle, curvature, volume, surface area, etc. as it is in the real gemstone. The geometric/coordinate relation/transformation between the fingerprint and the surface or volume model may be defined. For example, they may be defined in the same coordinate system.

As will be readily appreciated, a use of a gemstone fingerprint is to enable a gemstone to be uniquely identified with certainty and in a straightforward and repeatable manner. In order to achieve this, it is necessary that the fingerprint of any gemstone that is generated using the present invention is recorded and this recording can be used during subsequent scanning of the gemstone to confirm the gemstone's identity.

The fingerprint of a gemstone can be recorded in any manner apparent to a person skilled in the art. For example, the fingerprint of a gemstone can be recorded in a database along with other identifying information about the gemstone such as a unique identification number, scanning location and date, size, price, visual assessment data and/or any other suitable information. This database may be able to be accessed remotely via a network, for example via the internet.

When it is necessary to compare a gemstone against the database then the relevant gemstone will be scanned and a new fingerprint will be generated according to the method of the present invention. This new fingerprint will then be compared to the pre-existing fingerprints in the database and if a match is found then the gemstone can be positively identified.

As will be readily appreciated, the method by which the gemstone is subsequently scanned and the imaging apparatus used to carry out that scan may well differ from the method and apparatus originally used to generate the fingerprint. Therefore, the fingerprint generated in the subsequent scan may have more or less detail than the fingerprint that was initially generated. Nevertheless, the subsequent fingerprint should still be able to be easily matched with the initial fingerprint. This is because each fingerprint will still contain information about internal imperfections and their relevant location to one another. The information in the fingerprint with less detail will also be present in the fingerprint with more detail and this should allow them to be matched.

That is, in order to match a gemstone with a fingerprint in a database, it is not necessary to completely replicate the original fingerprint for that gemstone. All that is required is that the new fingerprint for the gemstone contains enough data for it to be matched to an existing fingerprint to a satisfactory level of confidence, for example 99.9% confidence or higher.

Optionally, the comparison of a new fingerprint of an unknown gemstone with a database can be carried in one of two modes. The gemstone can be checked against a single fingerprint within the database to determine whether that gemstone is a specific predetermined and previously scanned gemstone. Alternatively, the gemstone can be checked against every single fingerprint in the database. As will be readily appreciated, the first mode will be significantly quicker and may be all that is required if the user already has an idea about the identity of the gemstone. The second mode may be slower and may primarily be used for gemstones of unknown identity.

The matching of a new fingerprint with a fingerprint in a database can be done in any manner apparent to a person skilled in the art and will preferably be automated. For example, an adapted algorithm can be used based on cross-correlation, random or systematic feature checks, optimisation algorithms, pattern recognition or any other type of algorithm known in the field of signal and image processing. Such an algorithm may compute a confidence metric based on which the matching of two fingerprints can be established or excluded automatically or by the user.

The fingerprints generated by the present invention and any associated database may be used in any manner apparent to a person skilled in the art. One use may be for an industry wide tracking of gemstones, particularly diamonds, whereby existing and mined diamond has a fingerprint generated and is assigned an accompanying unique identifying number. This would allow the diamonds to be tracked as they are passed from a mine to a first customer and on to subsequent owners. As the fingerprint will allow a diamond to be identified, even if it is recut and/or re-polished this has the potential to provide a robust and fraud-proof method of tracking and identifying diamonds.

In addition or as an alternative to fingerprints, two-dimensional identification maps can be used to identify a gemstone in a more simple way, but having disadvantages listed above. Identification maps use the principal that if diffraction or extinction images are recorded in a fixed configuration, fixed geometry, acquisition method, acquisition parameters and crystal alignment, they can be reproduced at a later stage on the same or on a different apparatus, provided that all necessary parameters used for recording them are stored and known. Such records can be compared and a unique gemstone can be identified as the one with an existing record. The identification is still possible if there are small differences in the recording conditions or conditions with predictable or computable effects (e.g. geometric distortions, varying spatial resolution, etc.). The alignment of the gemstone can be defined and assured, for example, by using the outer surface of a gemstone and/or by using crystallographic axes of a gemstone.

When using the outer surface of a gemstone, the orientation and position of the gemstone is defined relative to a three-dimensional model of its outer surface. The model may be generated from a volume reconstruction that is obtained by absorption tomography or any adequate digital surface scanning method.

Alternatively, the surface or volume model can be reconstructed from the outlines of the gemstone in absorption or diffraction images. When the same alignment of a gemstone in an imaging apparatus is used for generating a fingerprint and a volume model, their relative position and orientation is straightforward to assure and compute. This can be achieved by performing the two measurements simultaneously or immediately one after the other on the same apparatus without unmounting or removing the gemstone from the sample holder or moving the gemstone relative to the sample holder. Alternatively, a reproducible alignment between the two recordings/scans can be enforced by mechanical, optical or other means on the same or on different apparatuses. The same considerations apply to creating a coordinated surface model of the gemstone.

A tomographic volume reconstruction can provide a highly detailed volume model for a large variety of shapes, including rough, uncut gemstones and concave surfaces. A highly detailed surface model can be created from a volume model by means known in the field of computer graphics or computer-aided design. Any adequate digital volume or surface representation known in the field can be used, such as a 3D array, polygon mesh, splines, Bézier surfaces, etc.

Flat faceted surfaces of gemstones, typically cut gemstones, can be represented by flat polygons, and optionally the facets can be defined specifically for certain cuts. In such representations, the position and orientation of each facet, or their deviations from a model of a standard or ideal cut is typically stored, which implicitly define all dimensions of the gemstone. In addition, certain dimensions of the gemstone, such as width, height, diameter, crown height, pavilion depth, crown angle, pavilion angle, etc. can be stored explicitly.

Jewellery is often made of noble or precious metals, for example, gold or platinum that are highly absorbing for x-rays, and give rise to diffraction due to their crystalline nature, which may contribute to the background noise in the images. When a gemstone is mounted in a piece of jewellery and it is desired to generate a fingerprint of that gemstone according to the method of the present invention the piece of jewellery may be able to be mounted in a sample holder of an imaging apparatus without removing the gemstone from the jewellery. In such cases, the jewellery has to be mounted in the sample holder such that, the incoming and outgoing beam paths are chosen in a way that the jewellery piece does not interfere with the scan or it interferes in a way that can be accounted for in the processing. In other words, the scanning strategy has to identify position and orientation combinations of the gemstone where extinction or diffraction images of parts of the gemstone can be detected. Gemstones in jewellery are usually cut and mounted in a way that they are well visible in a certain angular range. For example, engagement rings often have a simple geometry and contain a single gemstone which is visible from a large solid angle range. Appropriate access for the beam can, for example, be assured by providing mechanical mounting as part of the sample holder that can hold the jewellery piece rigidly and the gemstone can be positioned and orientated in a favourable way for the scan. In another example, particularly for a symmetric piece of jewellery containing one brilliant cut gemstone, the sample holder does not move during the scan and the gemstone is placed with its table facet downwards on a horizontal surface of the sample holder. The horizontal surface of the sample holder may be made of a material that is sufficiently transparent to the applied x-ray energies, preferably a single crystal or amorphous material, for the x-ray beam to pass through the holder during the scan.

In a preferred implementation of the method, a surface or volume model of a gemstone and the surrounding part of the jewellery piece is analysed to find an appropriate scanning strategy for the gemstone before the generation or reading of the fingerprint. In a preferred implementation, the surface or volume model is generated in the same apparatus as the fingerprint, by using x-ray absorption tomography and a volume reconstruction thereof. The surface or volume model of the gemstone is then used to find position and orientation combinations where extinction or diffraction images can be detected of parts of the gemstone, and they are sufficient for the generation or reading of the fingerprint over a certain region or over the entire gemstone.

The method of the present invention can be used to assess the quality and value of a gemstone. In particular, information on the imperfections of a crystal lattice contained in a fingerprint and in its combination with a surface or volume model of the gemstone, can be used to assess the carat weight, color, clarity, cut (4C) of a gemstone and thus the monetary value of a processed (cut) gemstone or of an unprocessed (rough) gemstone or gemstones resulting from it after cutting. The volume of the gemstone, its sub-regions or crystal within the gemstone can be determined from the intensity or outline in the diffraction, extinction or absorption images or from a volume reconstruction thereof. The weight (carat) can be computed from the volume using the density of the gemstone material. The cut quality of the gemstone depends on the accuracy of its geometry, i.e. primarily the dimensions of its facets and the angles between the facets when compared to a standard or ideal shape (cut). The quality of its polish, i.e. the surface quality, is also considered part of the cut quality.

As set out above, tomographic reconstructions and surface reconstruction thereof can provide high dimensional and angular accuracy to assess the shape of an object, and are used as means of metrology in production and quality control. When inspecting millimetre or centimeter sized objects, the spatial resolution can be down to or below one micrometer, and the angular accuracy can be $10^{-3}$ to $10^{-4}$ radians for flat surfaces. The quality of polish of a gemstone is higher for smoother surfaces, as a result, the quality of polish of a gemstone can be assessed from irregularities in the surface reconstruction of the facets. Alternatively, quality of polish can be assessed by aligning a given facet parallel to the direct x-ray beam, recording absorption images in the direct x-ray beam and analysing the intensity variations along and across the projection of the surface.

Alternatively or additionally, x-ray reflectometry analysis can be performed to record the intensity profile of reflected x-rays from the surface at grazing angles of incidence. Total external reflection occurs at and below the critical angle, and the intensity drops above the critical angle. The thickness, density and roughness of surface or near-surface layers can be measured from the intensity profile at the nanometer scale. This can be used to assess or quantify the quality of polish, and detect the presence of or identify coatings, ion implantation or other artificial surface treatments for a more comprehensive cut and color characterisation of a cut gemstone.

Alternatively or additionally, in case of adequate surface orientations relative to the underlying lattice, grazing incidence x-ray diffraction or grazing incidence small angle x-ray scattering can be used to probe the structure, morphology or directionality of surface layers to detect coatings, ion implantation and other artificial surface treatments.

The color of a gemstone is dependent on the chemical composition, structural defects and deformation of the lattice. For example, an important factor that determines the colour of a diamond is the amount of nitrogen impurities and optically active vacancy clusters. The fingerprint of a gemstone, particularly a diamond, can be used to detect structural defects that influence the colour of the gemstone or to detect structural defects and deformation states or fields which are correlated with certain colours of certain types of gemstones. As such the fingerprint of a gemstone can be used to assess the colour of the gemstone via such factors.

The clarity of a gemstone depends on the type, size, shape, composition, color and distribution of directly or indirectly visible internal defects, cracks, inclusions and deformation fields. Most of these factors can be quantified and a clarity assessment can be performed using the fingerprint either in isolation or in combination with additional information.

Recording the fingerprint of a gemstone in an audited procedure where at the time and place of extracting it at a mine can serve as proof of its natural origin.

An image or a movie showing the internal distinguishing features of the stone that is rendered from the fingerprint generated of the gemstone using any of the methods described above can be used in promoting or in marketing gemstones, and to engage potential customers with a specific gemstones.

When the fingerprint is generated in an audited procedure, it can be used to confirm the natural origin of the gemstone as a proof of location and circumstances of the extraction of the gemstone in a mining process. Similarly, it can be used to confirm the artificial/man-made/synthetic origin of the gemstone as a proof of location, manufacturer and circumstances of the production of the gemstone in a controlled industrial process.

Cutting design refers to the method and result of finding adequate procedures and the associated geometry for extracting one or multiple gemstones by separation and material removal from a given, typically unprocessed, gemstone. Cutting design of a gemstone can be performed and optimised based on information contained in a fingerprint of that gemstone. The goal of the optimisation can be, for example, to maximise the monetary value, weight, dimensions, clarity of one or more resulting gemstones, or to maximise the profitability of processing, processing efficiency, etc. The knowledge of the position and distribution of inclusions, cracks, lattice faults, crystal boundaries and the outer surface of the gemstone is often crucial to find the best cutting design. The additional knowledge of the deformation or strain state can be used to assess risks of damage that is introduced into the resulting gemstones during cutting, cleaving or sawing. This may involve finite element or simplified analytical methods to model and predict the strain/stress state and behavior of the crystals within the gemstone. For example, predictions can be based on changes of the elastic and surface energies in the proposed cutting procedures. The best cutting designs may be found and compared with an optimisation algorithm. The best cutting designs may then be stored digitally with the fingerprint, and used in an automatic cutting device or presented to the user.

Within the scope of the invention is a method whereby the fingerprint of a gemstone is analysed to directly assess the monetary value of the gemstone and optionally to assess additional information about the gemstone. Statistical analysis can be used to calibrate the value obtained according to this method with values based on standard gemstone inspection methods.

Fingerprints produced by the method of the present invention and their combination with additional information, such as the 4C quality assessment, may be used on rough gemstones in a fully automated process at a gemstone producing mine. Rapid feedback of information into the mineral processing enables handling different batches of the raw mineral in different ways to maximise the weight and/or quality yield at the end of the process.

The method of the present invention may be combined with further analysis methods. For example, a gemstone being analysed according to the method of the present invention may undergo UV fluorescence analysis, optical imaging of inclusions, and/or any other appropriate analysis whilst the gemstone is located in an imaging apparatus that is used to carry out the method of the present invention. The information obtained from any such analysis may or may not be used in the generation of the fingerprint.

Fluorescence in the visible, UV or x-ray range as a result of x-ray excitation of the gemstone can be used to characterise chemical properties, color and potential treatments that have been applied to the gemstone. X-ray fluorescence may be performed with the same detectors used for the fingerprinting in an energy discriminating mode. Detection of visible and UV wavelengths requires additional detector capability adapted to those wavelengths.

Photoluminescence, infrared, visible light, ultraviolet absorption spectroscopy, FTIR and Raman spectroscopy can be used to identify the cause of color in diamond, and to determine if it is naturally colored or treated. Photoluminescence in diamonds is highly sensitive to lattice defects, including vacancies, and to chemical composition, such as nitrogen content in the lattice. It is widely applied to detect synthetic diamonds and color treatment in diamonds.

The fingerprint may be combined with at least one pair of diffraction, absorption or phase contrast images that are recorded at an adequate angle to provide a fixed 3D stereoscopic view of internal microstructural features of the gemstone to a human observer.

The fingerprint can be complemented and correlated with typically low spatial resolution but distinctive compositional information within the gemstone obtained by spatially resolved x-ray fluorescence. To minimise measurement time, it may be applied only to specific locations where a potential inclusion has been detected. Three common methods to obtain spatially resolved fluorescence signals are:

1) using full beam excitation of the gemstone, and an energy resolving area detector with a pinhole aperture (like a camera obscura)
2) using full beam excitation of the gemstone, and an energy resolving area detector with optics (for example a polycapillary lens) that define the direction from which x-rays are received
3) using a single pixel energy resolving detector and a collimated or focused pencil beam for excitation.

Recording signals at different angular positions relative to the sample, three-dimensional chemical information can also be obtained.

In addition to a fingerprint, extinction or diffraction images can be recorded to provide equivalent two-dimensional cross-sections in fixed orientations of the gemstone, according to the methods described in U.S. Pat. No. 4,125,770 and/or WO 98/0801. The orientation of the gemstone is either defined relative to its crystal lattice orientation and/or its outer shape, surface or volume reconstruction. For certain types of cut gemstones, this may provide a potentially faster but less robust identification.

DRAWINGS

Figure 2:
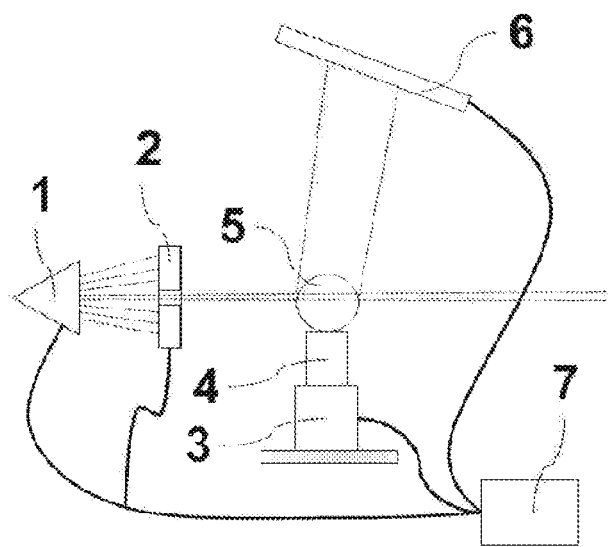

FIG. 1 is a schematic diagram of an imaging apparatus that may be used in a method according to the present invention; and FIG. 2 is a schematic diagram of an alternative imaging apparatus that may be used in a method of the present invention FIG. 1 shows an embodiment of an imaging apparatus that may be used in the method of the present invention. The imaging apparatus is a forward diffraction scanner and comprises an x-ray source 1, beam defining slits 2, a sample stage 3, a sample holder 4, a detector 6 and a processing unit 7. During use a gemstone 5 is mounted in the sample holder 4 which is mounted on the sample stage 3. The sample stage 3 can be controlled to vary the rotational position of the gemstone 5. The processing unit 7 controls and records position information from the x-ray source 1, the beam defining slits 2, the sample stage 3 and the detector 6, and the processing unit 7 receives recorded images from detector 6. In addition, the processing unit 7 receives and processes commands from a user or another unit, processes the recorded images and received data and information, determines a scanning strategy, generates a fingerprint and additional data, and transmits the fingerprint and additional data to a database.

The method of the present invention is carried out using the imaging apparatus in the following manner. First the gemstone 5 is mounted in the sample holder 4. There is no requirement for the gemstone 5 to be mounted in any specific orientation. Then the x-ray source 1 is controlled to emit a direct x-ray beam that propagates towards the beam defining slits 2. The beam defining slits 2 constrain the cross-section of the direct x-ray beam to irradiate the gemstone 5 and to shield the detector 6 from the direct x-ray beam. The direct x-ray beam leaving the beam defining slits 2 propagates towards and irradiates the gemstone 5. The sample stage 3 is controlled to vary the rotational position of gemstone 5 in a way that some of the irradiating direct x-ray beam is diffracted from a lattice plane in a crystal within the gemstone 5 towards the detector 6, which detects and records the resulting diffraction image. This is done according to a predetermined search strategy based on known physical characteristics of the gemstone 5, such as material. The processing unit 7 then uses the recorded diffraction images to generate a scanning strategy for the gemstone 5. The imaging apparatus is then controlled to carry out the generated scanning strategy and the resulting diffraction images are recorded by the detector 6 and sent to the processor. The processing unit 7 then generates a fingerprint for the gemstone from the diffraction images generated when the generated scanning strategy is carried out.

FIG. 2 shows an alternative imaging apparatus that can be used in the method of the present invention. The imaging apparatus of FIG. 2 is a section topography apparatus. The section topography apparatus comprises an x-ray source 1, beam defining slits 2, a sample stage 3, a sample holder 4, a detector 6 and a processing unit 7. During use a gemstone 5 is mounted in the sample holder 4.

When operated according to the method of the present invention. The x-ray source 1 is controlled to emit a direct x-ray beam, which propagates towards the beam defining slits 2 and the gemstone 5. The beam defining slits 2 constrain a cross-section of the direct x-ray beam to a narrow horizontal line at the position of gemstone 5. The direct x-ray beam reaches and irradiates a narrow section of the gemstone 5. The gemstone 5 is mounted on the sample holder 4 which is mounted on the sample stage 3. The sample stage 3 is controlled to change the rotational position of gemstone 5 relative to the direct x-ray beam in such a way that a narrow wavelength range in the irradiating direct x-ray beam is diffracted from a lattice plane in a section of a crystal within the gemstone 5. The diffracted x-ray beam propagates towards and is detected by the detector 6. The processing unit 7 controls and records position information from x-ray source 1, beam defining slits 2, sample stage 3 and detector 6, and the processing unit 7 records images from detector 6. In addition, the processing unit 7 receives and processes commands from a user or another unit, processes the recorded and received data and information, determines the scanning strategy, computes the fingerprint and additional data, and transmits the fingerprint and additional data to a database.

In the imaging apparatus of FIG. 2, the angle between the diffracted x-ray beam direction and the direct x-ray beam irradiating the gemstone 5 is around 90° (45° Bragg angle). The diffracted x-ray beam represents a projection of the irradiated section of the crystal. The method of the present invention is carried out using the imaging apparatus of FIG. 2 in substantially the same manner as the set out above for the imaging apparatus of Figure I with the exception that when the generated scanning strategy is carried out diffraction images (section topographs) are recorded from parallel sections of the crystal by translating the gemstone 5 perpendicular to the direct x-ray beam and the sections. Detector 6 records images in a synchronised manner with the translation of sample stage 3 and gemstone 5. This procedure is repeated for all crystals of interest within the gemstone 5. A fingerprint is then constructed from the imaged sections.

The invention claimed is:

1. A method of generating a fingerprint for a gemstone using x-ray imaging, wherein the fingerprint comprises a three-dimensional map of at least one crystal present within the gemstone including internal imperfections of the at least one crystal; the method comprising the steps of:

mounting the gemstone in a sample holder of an imaging apparatus, the imaging apparatus comprising a processing unit, a sample stage, a sample holder mounted on the sample stage, at least one x-ray source, and at least one detector, the sample holder and the at least one x-ray source aligned along an optical axis, wherein the sample holder is movable in at least one degree of freedom relative to the at least one x-ray source and the at least one detector;

exposing the mounted gemstone to x-ray radiation from the at least one x-ray source, while moving the sample holder relative to the at least one x-ray source and the at least one detector according to a search strategy that is predetermined for the gemstone based on known physical characteristics of the gemstone;

using the at least one detector to locate diffraction spots and/or extinction spots generated by a lattice of the at least one crystal;

utilizing the located diffraction spots and/or extinction spots to calculate information about a position, an orientation, and a phase of the at least one crystal;

generating a suitable x-ray diffraction scanning strategy from the calculated information, the suitable x-ray diffraction scanning strategy including moving the sample holder relative to the at least one x-ray source and the at least one detector and exposing the gemstone to appropriate x-ray radiation from the at least one x-ray source as the sample holder is moved, wherein the suitable x-ray diffraction scanning strategy is generated to observe a sufficient number and quality of diffraction images and/or extinction images for specified lattice planes of the at least one crystal to locate and classify internal imperfections of a crystal lattice of the at least one crystal;

scanning the gemstone according to the suitable x-ray diffraction scanning strategy and recording diffraction images and/or extinction images determined by the suitable x-ray diffraction scanning strategy using the at least one detector; and generating the fingerprint from the recorded diffraction images and/or extinction images;

wherein the processing unit controls the above steps of the method, and wherein the fingerprint comprises a map of the relative locations of more than five internal imperfections within the crystal in three dimensions.

2. A method according to claim 1, wherein the sample holder is movable in at least two degrees of freedom relative to the at least one x-ray source and the at least one detector.

3. A method according to claim 2, wherein the sample holder is movable in at least three degrees of freedom relative to the at least one x-ray source and the at least one detector.

4. A method according to claim 1, wherein the fingerprint further comprises a map of surface defects of the gemstone.

5. A method according to claim 1, wherein the fingerprint further comprises classification information about the internal imperfections.

6. A method according to claim 1, wherein the at least one x-ray source produces either a polychromatic spectrum or a monochromatic spectrum.

7. A method according to claim 1, wherein the suitable x-ray diffraction scanning strategy includes a topo-tomographic scan.

8. A method according to claim 1, wherein the imaging apparatus comprises a forward-diffraction scanner.

9. A method according to claim 1, wherein the sample stage has at least three degrees of translational freedom and three degrees of rotational freedom.

10. A method according to claim 1, wherein the imaging apparatus comprises one of:
a compact instrument, wherein the at least one detector comprises a fixedly-mounted high-resolution detector, wherein the at least one x-ray source comprises a fixedly-mounted polychromatic x-ray source that provides an effective source size smaller than 100 micrometers and a divergent beam, and wherein the sample stage is rotatable around at least two axes;
a section topography apparatus, wherein the at least one detector comprises a single detector that is positioned off the optical axis and is oriented toward the sample stage such that the single detector can detect diffracted x-ray beams from the gemstone such that an adequate spatial representation of a lattice defect within an irradiated section of the gemstone can be obtained; and
an x-ray tomography apparatus that records extinction spots in a direct x-ray beam and no diffraction spots.

11. A method according to claim 1, wherein the fingerprint contains information about an orientation and a location of the fingerprint relative to one or more of:

a surface model of the gemstone;
a volume model of the gemstone;
flat facets of the gemstone;
visible points of reference of the gemstone.

12. A method according to claim 1, wherein the fingerprint includes one or more of:
a direct grayscale reconstruction of an internal structure of the at least one crystal;
unclassified local defects of an internal structure of the at least one crystal;
classified local defects of an internal structure of the at least one crystal;
local defect statistics; and
information on strain, stress, or similar deformation fields within the at least one crystal.

13. A method according to claim 1, further comprising the steps of:
comparing the generated fingerprint with one or more of previously generated fingerprints;
wherein the comparing step comprises a correlation step, wherein the generated fingerprint is compared to the one or more of previously generated fingerprints using information on some or all of the internal imperfections in the generated fingerprint and a confidence metric is produced for a correlation between the generated fingerprint and the one or more previously generated fingerprints to identify the gemstone.

14. A method according to claim 1, further comprising the step of:
evaluating features of the generated fingerprint to determine whether the features are characteristic of a natural gemstone or a synthetic gemstone.

15. A method according to claim 1, further comprising the step of:
using evaluation features of the generated fingerprint to determine whether the gemstone has any features characteristic of one or more particular physical treatments in a current observed state of the gemstone, or when compared to a previously generated fingerprint of the gemstone to determine whether the gemstone has undergone a physical treatment.

16. A method according to claim 1, further comprising the steps of:
producing a three-dimensional computer model using the generated fingerprint; and
rendering of the gemstone by simulating a visual appearance of the gemstone and/or a three-dimensional fingerprint when viewed by a naked eye.

17. A method according to claim 1, further comprising the step of:
devising a cutting plan in reference to a three-dimensional digital computer model on a basis of the generated fingerprint of the gemstone for use in cutting a design of the gemstone.

18. A method according to claim 17, further comprising the step of:
combining information on the internal imperfections of the gemstone from the generated fingerprint with a surface model or a volume model of the gemstone to inform an assessment of a value of the gemstone.

19. A method according to claim 1, further comprising the step of:
combining information on the internal imperfections of the gemstone from the generated fingerprint with a surface model or a volume model of the gemstone to inform an assessment of a value of the gemstone.

20. A method according to claim 1, further comprising the step of:
- predicting current characteristics of a gemstone, or future characteristics of a gemstone following the cutting or other method of processing of the gemstone, from information in the generated fingerprint, where the current characteristics or the future characteristics include one or more of:
- a clarity of the gemstone;
- a cut quality of the gemstone;
- a color of the gemstone; and
- a carat weight of the gemstone.

21. A method according to claim 1, further comprising the step of:
- generating the fingerprint in an audited procedure; and
- confirming a natural origin of the gemstone as a proof of location and circumstances of an extraction of the gemstone in a mining process; or
- confirming an artificial/man-made/synthetic origin of the gemstone as a proof of location and circumstances of a production of the gemstone in a controlled industrial process.

* * * * *